(12) United States Patent
Maehr et al.

(10) Patent No.: US 8,853,248 B2
(45) Date of Patent: Oct. 7, 2014

(54) (1,2,3-TRIAZOLYL)SULFONYL DERIVATIVES

(76) Inventors: Hubert Maehr, Wayne, NJ (US);
Donchu Wei, Ellicott, MD (US)

( * ) Notice: Subject to any disclaimer, the term of this patent is extended or adjusted under 35 U.S.C. 154(b) by 0 days.

(21) Appl. No.: 13/440,113

(22) Filed: Apr. 5, 2012

(65) Prior Publication Data

US 2013/0267568 A1 Oct. 10, 2013

(51) Int. Cl.
*A01N 43/42* (2006.01)
*A61K 31/41* (2006.01)

(52) U.S. Cl.
USPC ........................................................ 514/359

(58) Field of Classification Search
CPC .. C07D 249/04; C07D 249/08; C07D 231/12; C07D 403/12; C07D 233/56
See application file for complete search history.

(56) References Cited

FOREIGN PATENT DOCUMENTS

EP       252640 A1 *    1/1988

OTHER PUBLICATIONS

Bandera, 4-Aryl(Benzyl)Sulfonyl-2-CHLOR0-5-Polyfluoroalkyl-1,2,3-Triazoles. The First Monocyclic N-Chloro-1,2,3-Triazoles, Chemistry of Heterocyclic Compounds, 2007, 43(9), pp. 1138-1147.*

English Translation of Georgiyants, Synthesis of the New Potential Anticonvulsants Among the Derivatives of 1-Aryl-4-(p-Alkylphenylsulfonyl)-5-Amino-1,2,3-Triazole (1 H), Zhurnal org. ta farm. khimiy, 2008, vol. 6, No. 3(23), p. 44-47.*

* cited by examiner

*Primary Examiner* — San-Ming Hui
*Assistant Examiner* — Andrew Lee

(57) ABSTRACT

The invention relates to a compound of the formula

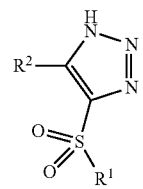

(1)

wherein the substituents are as defined herein, and pharmaceutically acceptable salts of the compound of formula (1). The compounds of formula (1), and their salts, possess inflammation inhibiting properties and are therefore useful in the treatment and prevention of conditions related to inflammations, such as inflammatory joint diseases, or other diseases caused by chronic inflammation. This application relates to compounds of formula (1), methods for their preparation, pharmaceutical compositions comprising these compounds and their use for the preparation of medicaments for the treatment of humans and animals.

14 Claims, No Drawings

# (1,2,3-TRIAZOLYL)SULFONYL DERIVATIVES

BACKGROUND

1. Field of the Invention

The invention relates to the field of anti-inflammatory drugs. More specifically, the invention relates to the use of compounds of formula (1) for the treatment and prevention of conditions related to inflammations, such as inflammatory joint diseases, and other diseases where inflammatory conditions are the underlying cause, and to methods for their preparation, medicaments comprising these compounds, and their use for the treatment of humans and animals.

2. Background and Description of Related Art

According to the Centers for Disease Control and Prevention, National Institute of Arthritis and Musculoskeletal and Skin Diseases, more than 40 million people in the US have some form of arthritis (one in every six people). It is estimated that by the year 2020, 59 million people in the United States will have arthritis. Rheumatic diseases are the leading cause of disability among persons age 65 and older. Approximately 20.7 million adults in the United States have the most common form of arthritis, osteoarthritis, also called degenerative joint disease. Most persons over the age of 75 are affected with osteoarthritis in at least one joint, making this condition a leading cause of disability in the US. Rheumatoid arthritis, the most crippling form of arthritis, affects approximately 2.1 million Americans and two to three times more women than men. The average onset for rheumatoid arthritis is between the ages of 20 and 45 years.

Since non-steroidal anti-inflammatory drugs (NSAIDs) are commonly prescribed by physicians and widely used by arthritis patients and those suffering from inflammation-related diseases, researchers and drug manufacturers team up to develop newer, safer, more effective choices. In accordance with this trend, the embodiment relates to new compounds of formula (1) that exhibit anti-inflammatory activity commonly observed among the members of the NSAID category of drugs. A compound of formula (1) is extremely effective in reducing and preventing inflammation and hence widens the treatment choices for the physician and the patient.

Certain prostaglandins are mediators of inflammations but are also implicated in areas other than inflammation-related conditions, such as cancer progression. In view of their effect on mitogenesis, cellular adhesion and apoptosis, prostaglandins play a major role in several types of cancers where an important cycloogygenase-2 (COX-2) expression has been demonstrated (Julémont, F., et al., J Med Chem 2004, 47, 6749). The different roles of lipoxygenases (LOXs) and their metabolic products in carcinogenesis and chemoprevention have been studied (Pommery, N., et al., J Med Chem 2004, 47, 6195). As examples, the effect of the 5-LOX/COX-2 inhibitor DMDMBF$_{30}$ showed promise as an inhibitor of the pancreatic cancer cell line Capan2 (Zhang, B. et al., World J Gastroenterol 2008, 14, 2494) and licofelone, a dual COX/5-LOX inhibitor, implemented apoptosis in HCA-7 colon cancer cells (Tavolari, S. et al., Carcinogenesis 2008, 29, 371). Celecoxib, a popular NSAID and a specific COX-2 inhibitor, was implicated in the inhibition of some nonmelanoma skin cancers (Elmets, C. A., J Natl Cancer Inst 2010, 102 (issue 24). Since NSAIDs inhibit COX-2/LOX in various ratios and degrees of efficiency, they can play a role in cancer prevention although COX-2 inhibition and anti-cancer effect may not be in direct correlation. Celecoxib, for example, was shown to induce apoptosis in prostate cancer cells but this effect was independent of the COX-2 inhibitory activity (Song, X., et al., J Natl Cancer Inst 2002, 94, 585).

The transcription factor NF-κB, the selective name for dimeric transcriptional modulators comprising the Rel family of proteins, has also been recognized to play a significant role in mediating inflammatory events through its ability to induce transcription of pro-inflammatory genes (Plummer S. M., et al., Oncogene, 1999, 18, 6013). Among the products, COX-2 and iNOS, the inducible isoform of nitric oxide synthase, are prime examples of enzymes that can change cell function, including the generation of inflammatory responses. iNOS is involved in immune responses and produces NO as a defense mechanism. It is the proximate cause of septic shock and may play a role in many diseases with an autoimmune etiology.

It has been shown that NF-κB is critical for the induction of COX-2 gene expression by TNFα in human colon tumor cells (Morteau, J. O., et al., Immunology 1998, 95, 537). Overexpression of COX-2 in colon epithelial cells, which occurs during colon carcinogenesis, causes resistance to apoptosis, suggesting that inhibition of NF-κB might reinstate susceptibility to apoptosis (Tsujii, M. and Dubois, R. N., Cell 1995, 83, 493). The ability to inhibit the NIK/IKK signaling complex, and hence preventing the activation of NF-κB, may be common to the action of some anti-inflammatory and chemopreventive agents. Aspirin and salicylates, known to inhibit phosphorylation and degradation of the IκB kinase enzyme complex (Kopp, E. and Ghosh, S., Science 1994, 265, 956), have been shown to inhibit the phosphorylation of IκB by specifically reducing ATP binding to IKKb (Yin, M. J, et al., Nature 1998, 396, 77) thus preventing the activation of NF-κB and potentially increasing chemosensitivity in many cancers (McCarty, M. F., Block, K. I., Integr Cancer Ther. 2006, 5, 252-268). The extensive involvement of Rel/NF-kB transcription factors in human inflammation and disease has established them as targets for therapeutics.

Many naturally occurring substances have anti-inflammatory activity and also exhibit chemopreventive effects on tumors. As per example, dietary flaxseed apparently prevents colon tumor development (Bommareddy, A., et al., Nutr Cancer 2006, 54, 216) and *Boswellia serrata* and ginger root extracts were used in the ancient Indian tradition of Ayervedic Medicine to control inflammation. The extract of *Boswellia serrata* was claimed to be superior to Valdecoxib in terms of safety, efficacy and duration of action (Sontakke, S., et al., Indian J Pharmacol 2007, 38, 27). Bromelain, derived from pineapples, is used to reduce post-operative swelling. Quercitin occurs naturally in many plants, most notably in red grapes, green tea, and onions and is used against a number of ailments wherein inflammation may be the underlying cause. Similarly, curcumin, the yellow pigment from turmeric, possesses anti-inflammatory and anti-oxidant activity (Ammon, H. R. T., et al., Planta Med 1991, 57, 1-7). It is also known as an anticarcinogenic agent and was studied extensively. It inhibits activation of NF-κB via the NIK/IKK signalling complex and thus exerts its activity by blocking many adverse reactions in which NF-κB plays a major role (U.S. Pat. No. 5,891,924, 1999). The hallmarks of these compounds are good anti-inflammatory activities, lack of stomach irritation and ulceration (Etzel R., Phytomed 1996, 3, 91) but only moderate inhibitory activities against isolated cycloogygenases.

Similar to these naturally occurring substances, compounds of formula (1) are also relatively weak inhibitors of isolated COX-1, COX-2, and 5-LOX enzymes. The apparent absence of gastrointestinal liabilities, their potent anti-inflammatory activity in vivo, as demonstrated by the adjuvant-induced arthritis test in rats, and their relatively weak activity in COX-specific in vivo tests, suggest a mode of action that differs from typical NSAIDs but resembles that of naturally occurring anti-inflammatory agents. A compound of the formula (1) is thus expected to be generally free of gastrointestinal disturbances and cardiovascular liabilities and to exhibit, in addition to anti-inflammatory action, chemopreventive activities in oncology, asthma, neurodegenerative diseases and heart diseases.

3. Prior Art

The object compounds of this embodiment are novel in a chemical and unusual in a pharmacological sense as they exert their biological function by a mechanism that is uncharacteristic of typical NASIDs.

BRIEF SUMMARY OF THE INVENTION

The embodiment relates to a compound of the formula

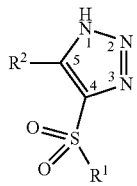

(1)

wherein $R^1$ is selected from aryl or a heterocyclic group which may be substituted at substitutable positions with one or more radicals selected from, but not limited to, the group comprising amino. cyano, halo, nitro, alkyl, deuteroalkyl, halo(lower) alkyl, hydroxyalkyl, aminoalkyl, (cycloalkyl)alkyl, alkoxyalkyl, carboxyalkyl, (alkoxycarbonyl)alkyl, alkoxycarbonyl(amino)alkyl, (aminosulfonyl)alkyl, (alkylsulfonyl)alkyl, (arylsulfonyl)alkyl, arylalkyl, alkenyl, arylalkenyl, aryl, heteroaryl, hydroxy, alkoxy, acyloxy, aroyloxy, carboxy, alkylcarbonyl, alkoxycarbonyl, arylcarbonyl, arylalkylcarbonyl, aminocarbonyl, (heterocyclic)carbonyl, aryloxycarbonyl, (heterocyclic)oxycarbonyl, alkylsulfanyl, alkylsulfinyl, alkylsulfonyl, aminosulfonyl, (alkylcarbonyl)aminosulfonyl, arylsulfonyl, and lower alkylsulfonyloxy;

$R^1$ may also be selected from, but not limited to, a group comprising alkyl, deuteroalkyl, cyanoalkyl, halo(lower) alkyl, hydroxyalkyl, alkoxyalkyl, amino(lower)alkyl, arylalkyl, aryloxyalkyl, (alkylcarbonyl)alkyl, (amino carbonyl)alkyl, (amino sulfonyl)alkyl, carboxyalkyl, alkoxycarbonylalkyl, alkoxycarbonyl(halo)alkyl, aminocarbonylalkyl, aminocarbonyl(halo)alkyl, heterocyclic (lower)alkyl, lower alkenyl, hydroxyl, lower alkoxy, deuteroalkoxy, haloalkoxy, and aryloxy;

$R^1$ may also be amino as represented by $NR^3R^4$, wherein $R^3$ may be hydrido, alkyl, deuteroalkyl, cyanoalkyl, halo (lower)alkyl, hydroxyalkyl, alkoxyalkyl, amino(lower) alkyl, aryl(lower)alkyl, alkylcarbonyl(lower)alkyl, aryl (lower)alkyl, lower alkenyl, hydroxy, lower alkoxy, deuteroalkoxy, aryloxy, aminoalkoxy, and $R^4$ is selected from, but not limited to, a group comprising hydrido, alkyl, deuteroalkyl, (cycloalkyl)alkyl, haloalkyl, hydroxyalkyl, alkoxyalkyl, alkylcarbonylalkyl, arylalkyl, aroylalkyl, aryloxyalkyl, heteroaryloxy (lower)alkyl, 5- or 6-membered heterocyclic alkyl, alkylcarbonylalkyl, alkoxycarbonylalkyl, aryloxycarbonylalkyl, heteroaryloxycarbonylalkyl, aminocarbonylalkyl, aminosulfonylalkyl, aminosulfonyl(amino)alkyl, carboxy(amino)alkyl, carboxy(halo) alkyl, alkoxycarbonyl(halo)alkyl, aminoalkyl, aminocarbonyl(halo)alkyl, heterocyclic(lower)alkyl, alkenyl, aryl substituted alkenyl, aryl or a 5- or 6-membered heterocyclic group, alkylcarbonyl, cycloalkylcarbonyl, alkoxycarbonyl, aminocarbonyl, arylcarbonyl, (heterocyclic)carbonyl, alkylsulfonyl, (cycloalkyl) alkylsulfonyl, arylsulfonyl, heteroarylsulfonyl, aminosulfonyl, and $R^3$ and $R^4$ taken together may be dialkylaminomethyleneamino, 1-(dialkylamino)ethylideneamino, or constitute a ring system that may include one or more additional heteroatoms, as in 1-piperidinyl, morpholino, 3-thiazolidinyl, 1,2,3-triazol-1-yl, and the like, and wherein the ring carbon atoms may be present in the form of carbonyl groups as in 2-piperidon-1-yl or 2,6-piperidinedion-1-yl;

$R^2$ is selected from, but not limited to, a group comprising aryl, heteroaryl or a heterocyclic group which may be substituted at substitutable positions with one or more radicals selected from, but not limited to, a group comprising amino, halo, cyano, nitro, alkyl, (cycloalkyl)alkyl, cyanoalkyl, deuteroalkyl, haloalkyl, hydroxyalkyl, aminoalkyl, alkoxyalkyl, arylalkyl, aryloxyalkyl, alkylcarbonylalkyl, aminocarbonylalkyl, aminosulfonylalkyl, aminosulfonyl(amino)alkyl, carboxyalkyl, alkoxycarbonylalkyl, aryloxycarbonylalkyl, carboxy(amino)alkyl, alkoxycarbonyl(amino)alkyl, aryloxycarbonyl(amino)alkyl, aminocarbonyl(amino)alkyl, carboxy(halo)alkyl, alkoxycarbonyl (halo)alkyl, alkoxycarbonyl(hydroxy)alkyl, aryloxycarbonyl(halo)alkyl, aminocarbonyl(halo)alkyl, heterocyclic (lower)alkyl, (heterocyclic)oxyalkyl, halo (lower)alkyl, lower alkenyl, arylalkenyl, aryl, heteroaryl, hydroxy, carboxy, alkoxy, haloalkoxy, deuteroalkoxy, acyloxy, aryloxy, heteroaryloxy, alkylcarbonyl, arylcarbonyl, heteroarylcarbonyl, (heterocyclic)carbonyl, arylalkylcarbonyl, alkoxycarbonyl, aryloxycarbonyl, (heterocyclic) oxycarboxyl, aminocarbonyl, lower alkylsulfanyl, lower alkylsulfinyl, lower alkylsulfonyl, arylsulfonyl, heteroarylsulfonyl, (cycloalkyl)alkylsulfonyl, aminosulfonyl, (aminomethylene)sulfamoyl, and lower alkylsulfonyloxy, and a pharmaceutically acceptable salt of a compound of formula (1).

The triazole ring in formula (1) may be representable in more than one tautomeric form, of which the representations (1) and (1a) are most significant:

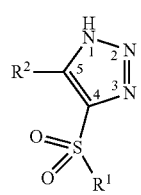

(1)

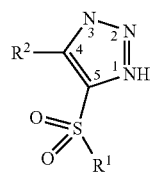

(1a)

For the sake of simplicity, we arbitrarily choose representation (1) as the predominant tautomeric form and apply this choice to all subsequent assignments of structures and nomenclature without additional comments. It should be emphasized that this choice does not exclude the possible preponderance of other tautomeric forms such as (1a).

The embodiment relates to new 5-substituted 4-(1,2,3-triazolyl)sulfonyl derivatives and pharmaceutically acceptable salts thereof. These compounds are useful for, but are not limited to, the treatment of inflammation in a subject, and other inflammation-associated disorders. The invention relates to processes for the preparation of said 5-substituted 4-(1,2,3-triazolyl)sulfonyl derivatives, to pharmaceutical compositions comprising the same, and to methods of using the same therapeutically in the treatment and/or prevention of diseases, especially inflammatory conditions, various pains, collagen diseases, autoimmune diseases, various immunity diseases and thrombosis in humans or animals, and more particularly to methods for the treatment and/or prevention of inflammation and pain in joint and muscle, e.g., rheumatoid arthritis, rheumatoid spondylitis, osteoarthritis, gouty arthritis, etc., inflammatory skin condition, e.g., sunburn, eczema, etc, inflammatory eye condition, e.g., conjunctivitis, etc., lung disorder in which inflammation is involved, e.g., asthma, bronchitis, pigeon fancier's disease, farmer's lung, etc, condition of the gastrointestinal tract associated with inflammation, e.g., aphthous ulcer, Crohn's disease, atropic gastritis, gastritis varialoforme, ulcerative colitis, coeliac disease, regional ileitis, irritable bowel syndrome, etc., gingivitis, inflammation, pain and tumescence after operation or injury, pain and other conditions associated with inflammation, particularly those in which LOX and COX products are a factor, diseases in which COX- and LOX-mediated metabolites play a procarcinogenic role, systemic lupus erythematosus, scleroderma, polymyositis, periarteritis nodosa, rheumatic fever, Sjögren's syndrome, Behcet disease, thyroiditis, type I diabetes, nephrotic syndrome, aplastic anemia, myasthenia gravis, uveitis, contact dermatitis, psoriasis, Kawasaki disease, sarcoidosis, Hodgkin's disease, and the like. Additionally, the object compounds are expected to be useful as therapeutic and/or preventive agents for conditions caused by overactivation of NF-kB, such as acute lymphoblastic leukemia, lymphomas, melanoma and other sarcomas, especially colon cancer. The object compounds are also expected to be useful for the treatment of cardiovascular or cerebrovascular diseases, liver disorders, and the diseases caused by hyperglycemia and hyperlipemia.

One object of the embodiment is to provide new and useful 5-substituted 4-(1,2,3-triazolyl)sulfonyl compounds of formula (1) and pharmaceutically acceptable salts thereof which possess antiinflammatory, analgesic, and antithrombotic activities.

Another object of this embodiment is to provide new and useful compounds of formula (1) and pharmaceutically acceptable salts thereof to counteract proliferation of tumor cells, especially as it pertains to colon cancer.

Another object of this embodiment is to provide a novel molecular scaffold for medicinal research in the form of compounds of formula (1), with the aim to find new medicines by applying combinatorial chemistry to the substituents $R^1$ and $R^2$ in the compound of formula (1), thus extending the pharmacological utility of a compound of formula (1). The methods for combinatorial chemistry are well known and have been described in the literature, for example in Maehr H., Bioorg Med Chem 1997, 5, 473.

Another object of the embodiment is to provide processes for the preparation of a compound of formula (1) and salts thereof.

Still further object of the embodiment is to provide a therapeutic method for the treatment and/or prevention of inflammatory conditions, various pains and the other diseases mentioned above, which consists of administering to a mammal, preferably a human, therapeutically effective amounts of a compound of formula (1).

Still further object of the embodiment is to provide therapeutically effective amounts of a compound of formula (1) in the manufacture of a medicament for the treatment of the disease conditions as outlined previously.

In another aspect, the embodiment relates to the usage of the compounds of formula (1), and their salts described above, for the treatment or prevention of inflammations and inflammation-related conditions, such as inflammatory joint disease, for example, arthritis.

In another aspect, the embodiment relates to pharmaceutical compositions which consist of a therapeutically effective amount of the compound of formula (1) or its pharmaceutically acceptable salt, together with a pharmaceutically acceptable carrier. Among them, the composition is preferably for the treatment of diseases mentioned above.

In another aspect, the embodiment relates to pharmaceutical compositions consisting of a solution or suspension, using a pharmaceutically acceptable carrier, of a compound of formula (1) described above.

In another aspect, the embodiment relates to the administration of a compound of formula (1) in a form suitable for the enteral or parenteral form of administration.

In yet another aspect, the embodiment relates to a method of administering a compound of formula (1) in the form of liposomes, in microencapsulated formulations, as nanoparticles, or in the form of emulsions or microemulsions.

In yet another aspect, the embodiment relates to a method of use of a compound of formula (1) in combination with stabilizing agents such as antioxidants.

In accordance with the methods of the invention, the compound of formula (1) can be administered in combination with a pharmaceutically acceptable carrier. In advantageous embodiments, the pharmaceutically acceptable carrier provides sustained delivery of the compound of formula (1) to a subject after administration to the subject. Alternatively, controlled release can be accomplished by pegylation as known to those skilled in the art.

In accordance with the methods of the invention, the compound of formula (1) can be administered in combination with water-soluble macromolecular entities, such as albumin or cyclodextrin and suitable derivatives thereof, or polyethylene glycol containing polymers, in order to improve their solubility, dissolution rate, taste-masking, bioavailability and/or stability for use in any of the aforementioned modes of administration. Recent advances in nanoformulation strategies, including nanostructured foams, can be used advantageously. Drug-cyclodextrin complexes, for example, are found to be generally useful for many dosage forms and administration routes. Both inclusion and non-inclusion complexes may be used. As an alternative to direct complexation with the drug, the cyclodextrin may be used as an auxiliary additive, i.e., as a carrier, diluent, or solubiliser. Most commonly used for these purposes are alpha-, beta- and gamma-cyclodextrins, and derivatives thereof, as exemplified by Harding, V. D., U.S. Pat. No. 6,632,803.

In accordance with the methods of the invention, the compound of formula (1) can be administered in various concentrations. The dosages may vary depending on the particular indication, route of administration, and the subject. Typically, the compound of formula (1) is administered orally at diurnal dosages of about 1 mg to 30 mg/kg of body weight.

In yet another aspect, the embodiment relates to the use of a compound of formula (1) in combination with other drugs that can augment the desired effect in a diseased subject.

In accordance with this embodiment, the treatment can be extended to viral infections by using a composition comprising an effective amount of a compound of formula (1), a local anesthetic, and an antiviral drug.

In connection with this embodiment the topical composition comprises an effective amount of a compound of formula (1), a local anesthetic such a benzocaine or lidocaine, and an antiviral drug selected from a group consisting of acyclovir, penciclovir, ganciclovir, a prodrug thereof or a combination thereof. The prodrug of the acyclovir comprises valacyclovir, and the prodrug of the penciclovir comprises famciclovir. The preparation of a formulation, comprising all ingredients in the form of a suitable gel or cream is known to those skilled in the art.

In accordance with this embodiment, the effective amount of the compound of formula (1), the local anesthetic, or the antiviral drug can be 0.1-20 wt %.

In another embodiment, the invention provides a packaged formulation which includes a pharmaceutical composition comprising a compound of formula (1) and a pharmaceutically acceptable carrier packaged with instructions for use in the treatment and prevention of conditions as outlined above.

In yet another aspect, the embodiment relates to a process for preparing a compound of the formula

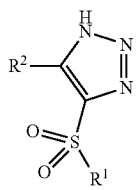

(1)

wherein the substituents $R^1$ and $R^2$ are selected from the definitions provided previously. The method consists of a reaction of a compound of the formula

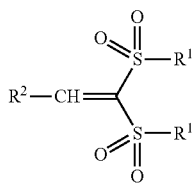

(2)

wherein the substituents $R^1$ and $R^2$ are as selected above, with a source of azide, such as a salt of hydrazoic acid, most conveniently with an inorganic salt of hydrazoic acid, such as sodium azide, in a polar solvent and at elevated temperature.

In yet another aspect, the embodiment relates to a process for preparing a compound of the formula (2). The method consists of a reaction between a compound of the formula

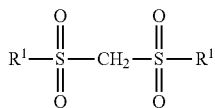

(3)

and a compound of formula $R^2$—CHO    (4)

wherein the substituents are as defined above. A compound of formula (4) may either be known or can be prepared by procedures known to those skilled in the art. The condensation is most conveniently accomplished under conditions related to Knoevenagel reaction conditions.

In yet another aspect, the embodiment relates to a method for preparing a compound of the formula

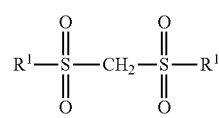

(3)

which is conveniently accomplished by oxidizing a compound of the formula $R^1$—S—$CH_2$—S—$R^1$    (5)

to the disulfone stage. The dithioacetals of formula (5) are either commercially available or may be prepared by procedures described in the literature and the oxidation can be brought about by a number of published procedures employing percarboxylic acids, hydrogen peroxide, persulfates, permanganates, and the like. Of these, persulfates in the form of Oxone (Trost, B. M. and Curran, D. P., Tetrahedron Lett 1981, 22, 1287) is usually preferred.

In yet another aspect, the embodiment relates to a process for preparing a compound of the formula

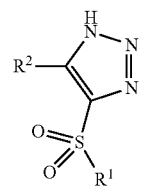

(1)

wherein the substituents are as defined above, by a cyclocondensation of a compound of the formula

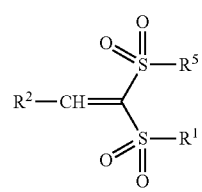

(2a)

with a hydrazoic acid salt. The methods diverges from the one previously described as the substituents $R^1$ and $R^5$ in formula (2a) differ from each other. In the cyclocondensation reaction of the compound of the formula (2a) only the $SO_2R^1$ group will be incorporated into the product while the group $SO_2R^5$ will be lost.

In yet another aspect, the embodiment relates to a method of preparing a compound of the formula (2a). The compound of formula (2a) can be prepared by a Knoevenagel-type condensation of an aldehyde of formula (4) with a disulfone of the formula

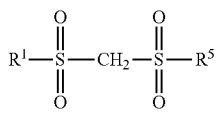
(3a)

wherein $R^1$ is selected from the group defined previously and $R^5$ is selected so that the group $SO_2R^5$ constitutes the better leaving group than $SO_2R^1$. The condensation reaction is analogous to the one described above, but the resulting bis-sulfonyl-vinyl arrangement of formula (2a) is usually obtained as a mixture of stereoisomers due to the inequality of $R^1$ and $R^5$. The requirement of $SO_2R^5$ as the better leaving group in the cyclocondensation of the compound (2a) is addressed in the construction of the compound (3a). This method is exemplified below.

In the aspect delineated above, the embodiment relates to a process of producing a compound of the formula

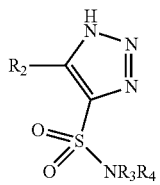
(1b)

wherein the substituent $R^2$, $R^3$, and $R^4$ are as defined previously. The method consists of a cyclocondensation of a compound of formula

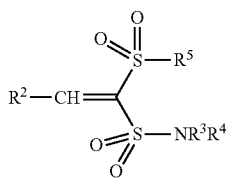
(2b)

wherein the substituents $R^2$, $R^3$, $R^4$ and $R^5$ are as defined previously, with a source of azide as described above, and wherein $R^5$=phenyl is preferred.

In yet another aspect, the embodiment relates to a method of synthesis of a compound of formula (2b) which consists of a reaction between a compound of the formula

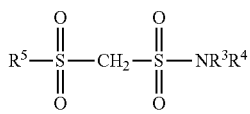
(3b)

wherein the substituents $R^3$, $R^4$ and $R^5$ are as defined above, with a compound of formula (4), analogous to methods described previously.

In yet another aspect, the embodiment relates to a method of preparing a compound of the formula (3b) from a compound of formula

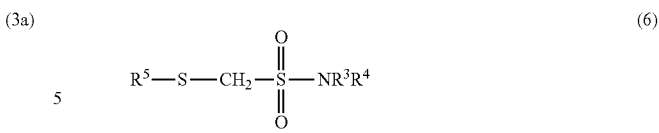
(6)

with a suitable oxidizing agent as laid out previously. The oxidation can be carried out analogous to the conditions described above.

In yet another aspect, the embodiment relates to a process of preparing a compound of the formula (6) which consists of subjecting a compound of formula

(7)

wherein the substituents $R^3$ and $R^4$ are as defined above and wherein X is a suitable leaving moiety, such as chlorine or bromine, to a thiolysis reaction using a suitable thiol in the presence of a suitable base and a polar solvent. Alternatively, a preformed salt of the thiol can be used. The use of the commercially available sodium thiophenolate, in the presence of 2-propanol as solvent, is preferred.

The compound of formula (7) wherein X is chloro, is conveniently prepared from commercially available chloromethanesulfonyl chloride by treatment with a suitable primary or secondary amine. Depending on the nature of the amine, the amine may be employed as the free base or as a salt in the presence of a suitable base and an inert solvent.

In yet another aspect, the embodiment relates to a process for preparing a compound of the formula

(1)

wherein the substituent $R^2$ is as defined previously and $R^1$ is selected from a group defined previously, by oxidizing a compound of the formula

(1c)

wherein the substituent $R^2$ is as defined above. The divalent sulfur is conveniently converted to the sulfonyl stage by any of the suitable oxidative processes mentioned previously.

In yet another aspect, the embodiment relates to a method of preparation of a compound of formula (1c) by a cyclocondensation of a compound of formula

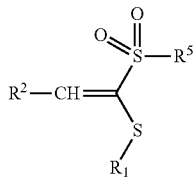

(2c)

wherein the substituent $R^1$ and $R^2$ are as defined above and the group $SO_2R^5$ constitutes the designated leaving group, with a suitable salt of hydrazoic acid as laid out previously.

In yet another aspect, the embodiment relates to a method of preparing a compound of the formula (2c) by a Knoevenagel-type condensation of an aldehyde of the formula 4 with a compound of the formula

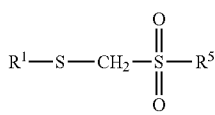

(6a)

wherein $R^1$ is as defined above and $SO_2R^5$ is a suitable leaving group, such as phenylsulfonyl.

In yet another aspect, the embodiment relates to a process of preparing a compound of the formula (6a) which consists of subjecting a compound of formula

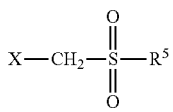

(7a)

wherein X is as defined above, to thiolysis reaction conditions. A suitable compound of formula (7a) is the commercially available chloromethanesulfonylbenzene. The reaction is accomplished by a nucleophilic displacement of the halogen moiety in (7a) with a suitable thiol of the formula $R^1SH$, using methods delineated previously.

In yet another aspect, the embodiment relates to a process for preparing a compound of the formula

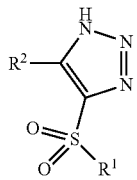

(1)

wherein the substituents $R^1$ and $R^2$ are as defined previously, by oxidizing a compound of the formula

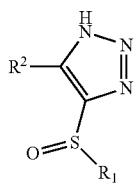

(1d)

wherein the substituents $R^1$ and $R^2$ are as defined above. The tetravalent sulfur in substituent $SOR^1$ is conveniently converted to the sulfonyl stage by a suitable oxidative process mentioned above.

In yet another aspect, the embodiment relates to a method of preparation of a compound of formula (1d) by a cyclocondensation of a compound of formula

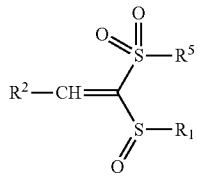

(2d)

wherein the substituents $R^1$ and $R^2$ are as defined above and the group $SO_2R^5$ constitutes a suitable leaving group. The appropriate reaction conditions have been described previously.

In yet another aspect, the embodiment relates to a method of preparing a compound of the formula (2d) by a Knoevenagel-type condensation of an aldehyde of the formula (4) with a compound of the formula

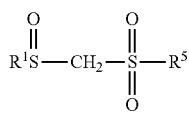

(6b)

wherein the substituent $R^1$ is as described above and the group $SO_2R^5$ constitutes a suitable leaving group in the subsequent cyclocondensation reaction. The appropriate reaction conditions for the Knoevenagel-type condensation have been described previously.

A compound of the formula (6b) can be prepared from a compound of the formula

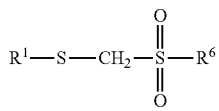

(6a)

by a selective oxidative process, using reagents such as periodic acid, or one equivalent of m-chloroperbenzoic acid in a suitable solvent such as dichloromethane, for example.

The advantage of the compounds of the types (2c) and (2d), wherein the substituents $R^1$ are connected to divalent and tetravalent sulfur, respectively, consist in the enhanced ability of the group $SO_2R^5$ to function as leaving group in the cyclocondensation step leading, after further oxidation, to a compound of formula (1).

DETAILED DESCRIPTION OF THE INVENTION

The embodiment relates to a compound of the formula

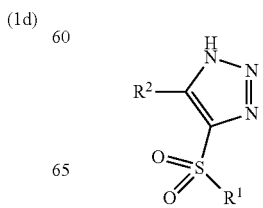

(1)

wherein
- R¹ is selected from aryl or a heterocyclic group which may be substituted at substitutable positions with one or more radicals selected from, but not limited to, the group comprising amino. cyano, halo, nitro, alkyl, deuteroalkyl, halo(lower)alkyl, hydroxyalkyl, aminoalkyl, (cycloalkyl)alkyl, alkoxyalkyl, carboxyalkyl, (alkoxycarbonyl)alkyl, alkoxycarbonyl(amino)alkyl, (aminosulfonyl)alkyl, (alkylsulfonyl)alkyl, (arylsulfonyl)alkyl, arylalkyl, alkenyl, arylalkenyl, aryl, heteroaryl, hydroxy, alkoxy, acyloxy, aroyloxy, carboxy, alkylcarbonyl, alkoxycarbonyl, arylcarbonyl, arylalkylcarbonyl, aminocarbonyl, (heterocyclic)carbonyl, aryloxycarbonyl, (heterocyclic)oxycarbonyl, alkylsulfanyl, alkylsulfinyl, alkylsulfonyl, aminosulfonyl, (alkylcarbonyl)aminosulfonyl, arylsulfonyl, and lower alkylsulfonyloxy;
- R¹ may also be selected from, but not limited to, a group comprising alkyl, deuteroalkyl, cyanoalkyl, halo(lower)alkyl, hydroxyalkyl, alkoxyalkyl, amino(lower)alkyl, arylalkyl, aryloxyalkyl, (alkylcarbonyl)alkyl, (amino carbonyl)alkyl, (amino sulfonyl)alkyl, carboxyalkyl, alkoxycarbonylalkyl, alkoxycarbonyl(halo)alkyl, aminocarbonylalkyl, aminocarbonyl(halo)alkyl, heterocyclic(lower)alkyl, lower alkenyl, hydroxyl, lower alkoxy, deuteroalkoxy, haloalkoxy, and aryloxy;
- R¹ may also be amino as represented by NR³R⁴, wherein
  - R³ may be hydrido, alkyl, deuteroalkyl, cyanoalkyl, halo(lower)alkyl, hydroxyalkyl, alkoxyalkyl, amino(lower)alkyl, aryl(lower)alkyl, alkylcarbonyl(lower)alkyl, aryl(lower)alkyl, lower alkenyl, hydroxy, lower alkoxy, deuteroalkoxy, aryloxy, aminoalkoxy, and
  - R⁴ is selected from, but not limited to, a group comprising hydrido, alkyl, deuteroalkyl, (cycloalkyl)alkyl, haloalkyl, hydroxyalkyl, alkoxyalkyl, alkylcarbonylalkyl, arylalkyl, aroylalkyl, aryloxyalkyl, heteroaryloxy(lower)alkyl, 5- or 6-membered heterocyclic alkyl, alkylcarbonylalkyl, alkoxycarbonylalkyl, aryloxycarbonylalkyl, heteroaryloxycarbonylalkyl, aminocarbonylalkyl, aminosulfonylalkyl, aminosulfonyl(amino)alkyl, carboxy(amino)alkyl, carboxy(halo)alkyl, alkoxycarbonyl(halo)alkyl, aminoalkyl, aminocarbonyl(halo)alkyl, heterocyclic(lower)alkyl, alkenyl, aryl substituted alkenyl, aryl or a 5- or 6-membered heterocyclic group, alkylcarbonyl, cycloalkylcarbonyl, alkoxycarbonyl, aminocarbonyl, arylcarbonyl, (heterocyclic)carbonyl, alkylsulfonyl, (cycloalkyl)alkylsulfonyl, arylsulfonyl, heteroarylsulfonyl, aminosulfonyl, and
  - R³ and R⁴ taken together may be dialkylaminomethyleneamino, 1-(dialkylamino)ethylideneamino, or constitute a ring system that may include one or more additional heteroatoms, as in 1-piperidinyl, morpholino, 3-thiazolidinyl, 1,2,3-triazol-1-yl, and the like, and wherein the ring carbon atoms may be present in the form of carbonyl groups as in 2-piperidon-1-yl or 2,6-piperidinedion-1-yl;
- R² is selected from, but not limited to, a group comprising aryl, heteroaryl or a heterocyclic group which may be substituted at substitutable positions with one or more radicals selected from, but not limited to, a group comprising amino, halo, cyano, nitro, alkyl, (cycloalkyl)alkyl, cyanoalkyl, deuteroalkyl, haloalkyl, hydroxyalkyl, aminoalkyl, alkoxyalkyl, arylalkyl, aryloxyalkyl, alkylcarbonylalkyl, aminocarbonylalkyl, aminosulfonylalkyl, aminosulfonyl(amino)alkyl, carboxyalkyl, alkoxycarbonylalkyl, aryloxycarbonylalkyl, carboxy(amino)alkyl, alkoxycarbonyl(amino)alkyl, aryloxycarbonyl(amino)alkyl, aminocarbonyl(amino)alkyl, carboxy(halo)alkyl, alkoxycarbonyl(halo)alkyl, alkoxycarbonyl(hydroxy)alkyl, aryloxycarbonyl(halo)alkyl, aminocarbonyl(halo)alkyl, heterocyclic (lower)alkyl, (heterocyclic)oxyalkyl, halo(lower)alkyl, lower alkenyl, arylalkenyl, aryl, heteroaryl, hydroxy, carboxy, alkoxy, haloalkoxy, deuteroalkoxy, acyloxy, aryloxy, heteroaryloxy, alkylcarbonyl, arylcarbonyl, heteroarylcarbonyl, (heterocyclic)carbonyl, arylalkylcarbonyl, alkoxycarbonyl, aryloxycarbonyl, (heterocyclic)oxycarboxyl, aminocarbonyl, lower alkylsulfanyl, lower alkylsulfinyl, lower alkylsulfonyl, arylsulfonyl, heteroarylsulfonyl, (cycloalkyl)alkylsulfonyl, aminosulfonyl, (aminomethylene)sulfamoyl, and lower alkylsulfonyloxy, and a pharmaceutically acceptable salt of a compound of formula (1).

In the above and subsequent description of the present specification, suitable examples of the various definitions to be included within the scope of the invention are explained in detail below.

The term "lower" is intended to mean a group having 1 to 6 carbon atoms.

As used herein, the term "halo" means fluoro, chloro, bromo, or iodo, of which fluoro and chloro are preferred.

The term "amino" denotes an amino group that may be unsubstituted or it may have the form of NR³R⁴ as described above, as in 4-pyridinylamino, anilino, morpholino, diphenylamino and N-alkyl-1H-indol-3-amino, or example; of these methylamino is preferred.

The term "alkyl" denotes methyl, or a straight, saturated hydrocarbon moiety, such as ethyl, n-propyl, n-butyl, and the like, or an alkyl substituted alkyl in the form of a branched hydrocarbon chain as in isopropyl, neopentyl and the like; of these, methyl and tert-butyl are preferred. The term also includes cycloalkyl in the form of a saturated carbocyle containing 3 to 6 carbon atoms, such cyclopropyl, cyclobutyl, and cyclohexyl, for example, of which cyclopropyl is preferred.

The term "(cycloalkyl)alkyl" denotes a cycloalkyl substituted alkyl as in (cyclohexyl)ethyl for example; of these (cyclopropyl)methyl is preferred.

The term "deuteroalkyl" denotes a partially or fully deuterated methyl, such as trideuteromethyl, or a lower alkyl, substituted with one or more deuterium atoms, such as 2,2,2-trideuteroethyl, pentadeuteroethyl and the like; of these trideuteromethyl is preferred.

The term "hydroxyalkyl" denotes a hydroxy substituted alkyl such as hydroxyethyl, 2,3-dihydroxypropyl, and the like; of these 2-hydroxyethyl is preferred.

Suitable "haloalkyl" are halo-substituted alkyls and may be chloromethyl, trifluoromethyl, 2-fluoroethyl, 4-chlorobutyl, and the like, of which trifluoromethyl is preferred.

The term "alkoxyalkyl" denotes an alkoxy substituted alkyl, such as a methoxymethyl and 3-methoxyprop-1-yl, or an alkyl radical substituted with one or more alkoxy residues as in 3,5-dimethoxy-hex-1-yl, and the like.

The term "arylalkyl" is an aryl substituted alkyl wherein aryl is as defined below; suitable examples are 2,2-diphenylethyl, phenethyl, 2-(3-fluorophenyl)ethyl, of these benzyl is preferred.

The term "aryloxyalkyl" denotes an alkyl moiety substituted by one or more aryloxy residue wherein the aryl groups are as defined below, such as phenoxymethyl or 2-[(1-methyl-4-piperidyl)oxy]ethyl, and the like.

The term "alkylcarbonylalkyl" denotes an alkanoylalkyl as in 2-oxo-1-butyl for example; of these 3-methyl-2-oxo-1-butyl is preferred.

The term "alkylsulfonylalkyl" denotes an alkyl group, substituted with alkylsulfonyl, as in (methylsulfonyl)methyl or 3-(ethylsulfonyl)-1-propyl, for example.

The term "alkoxycarbonylalkyl" denotes an alkyl substituted with one or more alkoxycarbonyl residues, of which (ethoxycarbonyl)methyl is preferred.

The term "alkoxycarbonyl(amino)alkyl" is an alkyl substituted with alkoxycarbonyl and one or more amino groups; of these 2-amino-3-ethoxy-3-oxo-propyl is preferred.

The term "alkoxycarbonyl(halo)alkyl" is an alkyl substituted with alkoxycarbonyl and one or more halo substituents as in 2-ethoxycarbonyl-2,2-difluoroethyl, for example.

The term "alkoxycarbonyl(hydroxy)alkyl" is an alkyl substituted with alkoxycarbonyl and one or more hydroxy groups, as in 4-hydroxy-5-methoxy-5-oxo-pentyl, for example.

The term "carboxy(halo)alkyl" denotes an alkyl substituted with one or more carboxy and one or more halo substituents.

The term "(heterocyclic)alkyl" denotes an alkyl group substituted with a heterocyclic group, as in (2-pyridyl)methyl or bis(4-pyridyl)methyl, for example.

The term "(heterocyclic)oxyalkyl" is a heterocyclic group linked to an alkyl group through an oxygen linkage, as in 2-((4-piperidyl)oxy)ethyl, for example.

The term "carboxy(amino)alkyl" denotes an alkyl group, that is substituted with one or more carboxy and amino radicals; of these 2-carboxy-2-amino-ethyl is preferred.

The term "aminoalkyl" is an alkyl substituted with one or more amino groups as defined above, such as 2,3-diaminopropyl or 2-[1-hydroxy(methyl)amino]ethyl, for example.

The term "aminocarbonylalkyl" denotes an alkyl substituted with a carbamoyl group as in 6-dimethylamino-6-oxohexyl, or 3-amino-3-oxo-prop-1-yl, for example.

The term "aminocarbonyl(halo)alkyl" is an alkyl substituted with carbamoyl and one or more halo substituents as in 4-(dimethylamino)-3,3-difluoro-4-oxo-butyl, for example.

The term "aminocarbonyl(amino)alkyl" is an alkyl substituted with carbamoyl and amino, as in 4,5-diamino-5-oxopentyl, for example.

The term "aminocarbonyl(hydroxy)alkyl" is an alkyl substituted with hydroxyl and carbamoyl, as in 4-hydroxy-5-(methylamino)-5-oxo-pentyl, for example.

The term "aminosulfonylalkyl" denotes an alky moiety substituted with a sulfamoyl group as in N,N-dimethylaminosulfonylethyl; of these (acetylsulfamoyl)methyl is preferred.

The term "amino(halo)alkyl" is an alkyl bearing an amino group as defined previously and one or more halo substitutes, for example 2-(diethylamino)-1,1,2,2-tetrafluoroethyl.

The term "carboxy(amino)alkyl" denotes an alkyl group bearing an amino and a carboxy group; of these (2-carboxy-2-amino)ethyl is preferred.

The term "alkenyl" denotes an unsaturated alkyl such as ethenyl, 2-propenyl, and 2-butenyl; of these 1-propenyl is preferred.

The term "arylalkenyl" means an aryl substituted alkenyl such as styryl, cinnamyl, 2-(4-acetylphenyl)ethenyl, and the like.

Suitable "aryl" may be an aromatic moiety such as phenyl, naphthyl, and the like, of which phenyl is preferable. The term "aryl" also denotes substituted aryl groups wherein the substituents are chosen from, but not limited to those defined previously for $R^2$; of these 3,5-di-tert-butyl-4-hydroxyphenyl is preferred.

The term "heterocyclic" or "heterocyclic group" includes "heteroaryl" and includes saturated or unsaturated, monocyclic or polycyclic groups containing at least one hetero atom such as nitrogen, oxygen or sulfur. The preferred examples of thus defined "heterocyclic group" may be unsaturated, 3 to 8-membered, more preferably 5- or 6-membered heteromonocyclic groups containing 1 to 4 nitrogen atoms, for example, pyrrolyl, imidazolyl, pyrazolyl, pyridyl, pyridyl N-oxide, dihydropyridyl, tetrahydropyridyl, pyrimidyl, pyrazinyl, pyridazinyl, triazinyl, triazolyl, tetrazinyl, tetrazolyl, etc.; or saturated, 3 to 8-membered, more preferably 5 or 6-membered, heteromonocyclic groups containing 1 to 4 nitrogen atoms, for example, pyrrolidinyl, imidazolidinyl, piperidino, piperazinyl, etc.; or unsaturated, condensed heterocyclic groups containing 1 to 5 nitrogen atoms, for example, indolyl, isoindolyl, indolizinyl, benzimidazolyl, quinolinyl, isoquinolinyl, indazolyl, benzotriazolyl, etc.; or unsaturated, 3 to 8-membered heteromonocyclic groups containing 1 to 2 oxygen atoms, and 1 to 3 nitrogen atoms, for example, oxazolyl, isoxazolyl, oxadiazolyl, etc.; or saturated, 3 to 8-membered heteromonocyclic groups containing 1 to 2 oxygen atoms and 1 to 3 nitrogen atoms, for example, morpholino, sydnonyl, etc.; or unsaturated, condensed heterocyclic groups containing 1 to 2 oxygen atoms and 1 to 3 nitrogen atoms, for example, benzoxazolyl, benzoxadiazolyl and the like, or unsaturated, 3 to 8-membered heteromonocyclic groups containing 1 to 2 sulfur atoms and 1 to 3 nitrogen atoms, for example, thiazolyl, isothiazolyl, thiadiazolyl, etc.; or unsaturated, 3 to 8-membered heteromonocyclic groups containing 1 to 2 sulfur atoms, for example, thienyl, etc.; or unsaturated condensed heterocyclic groups containing 1 to 2 sulfur atoms and 1 to 3 nitrogen atoms, for example, benzothiazolyl, benzothiadiazolyl, etc.; or unsaturated, 3 to 8-membered heteromonocyclic groups containing an oxygen atom, for example, furyl, etc.; or unsaturated, condensed heterocyclic groups containing 1 to 2 sulfur atoms, for example, benzothienyl, etc.; or unsaturated, condensed heterocyclic groups containing 1 to 2 oxygen atoms, for example, benzofuranyl, and the like; of these 4-hydroxy-3-indolyl, 6-methoxy-4-quinolinyl, and 4,6-di-tert-butyl-5-hydroxy-pyrimidine-2-yl are preferred.

Suitable "alkoxy" are methoxy, ethoxy, isopropoxy, tert-butoxy and the like, in which the preferable one is methoxy; the term also includes carbocyclic alkoxy such as cyclopentyloxy.

The term "deuteroalkoxy" denotes an alkoxy residue wherein some or all of the hydrogen atoms are replaced by deuterium; of these trideuteromethoxy is preferred.

The term "haloalkoxy" means a halo-substituted alkoxy such as 2,2,2-trifluoroethoxy and 2,2-difluoroethoxy; of these 2-fluoroethoxy is preferred.

The term "aminoalkoxy" denotes an alkoxy residue wherein the alkyl is substituted with amino, and wherein the O and N atoms are separated by at least two carbon atoms as in 2-(N,N-dimethylamino)ethoxy.

The term "acyloxy" is synonymous with alkylcarbonyloxy and alkanoyloxy and denotes an acyl group linked to oxygen, as in acetoxy, for example.

The term "aroyl" denotes a carbonyl group attached to an aryl moiety as defined above, such as 6-methoxy-2-naphthoyl for example, of these benzoyl is preferred.

The term "aryloxy" denotes an aryl residue linked to oxygen, such as 4-fluorophenoxy.

The term "(heterocyclic)oxy" denotes a heterocyclic group linked to oxygen, such as 2-furyloxy.

The term "aroyloxy" denotes an aroyl group linked to oxygen, as in benzoyloxy.

The term "aminocarbonyl" denotes a carbamoyl group whose nitrogen atom may take the form of $NR^3R^4$ as defined previously.

The term "arylcarbonyl" denotes a carbonyl group substituted by an aryl group, such as 2-fluorobenzoyl, and the like.

The term "alkylcarbonyl" means "acyl or alkanoyl" and denotes a carbonyl group substituted by an alkyl moiety as defined previously, including hydrido, as in formyl, acetyl, secondary butyryl and cyclopropylcarbonyl, for example.

Suitable "(heterocyclic)carbonyl" are heterocyclic moieties attached to carbonyl, such as imidazolidinylcarbonyl, piperidinocarbonyl, nicotinoyl, and piperazinylcarbonyl; of these pyrrolidinylcarbonyl is preferred.

The term "alkoxycarbonyl" means a carbonyl group substituted with an alkoxy group as defined previously; of these ethoxycarbonyl is preferred.

The term "aryloxycarbonyl" means a carbonyl group substituted with an aryloxy group as defined previously, for example phenoxycarbonyl.

The term "arylalkylcarbonyl" denotes a carbonyl group bearing an arylalkyl moiety such as phenethyloxycarbonyl for example; of these benzyloxycarbonyl is preferred.

The term "(heterocyclic)oxycarbonyl" means a carbonyl group substituted with a heterocyclic group via an oxygen linkage such as ((2-(pyridinyl)oxy)carbonyl for example.

The term "aminocarbonyl" denotes a carbamoyl group whose amino group is as defined previously, such as morpholinocarbonyl, for example.

The term "aminosulfonyl" denotes a sulfamoyl group wherein the amino group is as defined previously, for example methylsulfamoyl, propanoylsulfamoyl, and the like; of these sulfamoyl and acetylsulfamoyl are preferred.

The term "(aminomethylene)sulfamoyl" is an $R^3R^4N-CR=N-SO_2-$ moiety wherein $R^3$ and $R^4$ are as defined previously and R may be hydrido or lower alkyl; of these N N-(dimethylaminomethylene)sulfamoyl is preferred.

Suitable "alkylsulfonyl" are methylsulfonyl, propylsulfonyl and the like; of these the preferable one is methylsulfonyl.

Suitable "(cycloalkyl)alkylsulfonyl" are (cyclopropyl)methylsulfonyl and (cyclopentyl)methylsulfonyl for example.

The term "arylsulfonyl" denotes a sulfonyl group substituted with aryl, such as p-tolylsulfonyl, and the like.

The term "(heterocyclic)sulfonyl" denotes a sulfonyl group substituted with a heterocyclic group; of these (2-pyridyl)sulfonyl is preferred.

Suitable "alkylsulfinyl" may be methylsulfinyl, ethylsulfinyl and the like, of these methylsulfinyl is preferred.

Suitable "alkylsulfanyl" include methylsulfanyl and ethylsulfanyl, of which methylsulfanyl is preferred.

Suitable pharmaceutically acceptable salts of the object compound (1), containing molecular groups with basic or acidic character, are conventional non-toxic salts and include acid addition salts such as an inorganic acid addition salt, for example a hydrochloride, hydrobromide, sulfate, phosphate, etc., an organic acid addition salt such as acetate, trifluoroacetate, maleate, tartrate, methanesulfonate, benzenesulfonate, toluenesulfonate, etc., a salt with an amino acid such as arginine salt, aspartic acid salt, glutamic acid salt, etc., a metal salt such as an alkali metal salt, for example a sodium salt, potassium salt, etc., and an alkaline earth metal salt such as a calcium salt or magnesium salt, etc., an ammonium salt, an organic base addition salt such as trimethylamine salt, triethylamine salt, etc., and the like.

The term "effective amount" includes an amount effective, at dosages and for periods of time necessary, to achieve the desired result, e.g., an anti-inflammatory response, for example the reduction of swelling of a joint. An effective amount of a compound of formula (1) may vary according to factors such as the disease state, age and weight of the subject, and the ability of the compound of formula (1) to elicit a desired response in the subject. Dosage regimens may be adjusted to provide the optimum therapeutic response. An effective amount is also one in which any undesirable side effects are outweighed by the therapeutically beneficial effects.

The term "treatment" as used herein, refers to impeding, reversing, alleviating, inhibiting or preventing the disorder, or the pathological condition, to which such term applies.

The term "therapeutically effective amount" describes the amount of a compound of formula (1) to elicit a desirable effect. This amount can be administrated by enteral or parenteral routes. Diurnal dosages may range from about 1 to 50 mg/kg of body weight; for oral administration a dose between about 3 to 10 mg/kg body weight is preferred. The actual daily dose and the duration of treatment will be a function of the mode of administration of the drug and the nature of the subject, such as the severity of the disease or disorder, previous treatments, the general health and/or age of the subject, other diseases present, and other current medicaments prescribed. Moreover, treatment of a subject with a therapeutically effective amount of a compound of formula (1) can include a single treatment or, preferably, can include a series of treatments. In one example, a subject is treated daily with an oral dose of a compound of formula (1) for a two week period using a drug concentration of 5 mg/kg body weight for each administration. It will also be appreciated that the effective dosage of a compound of formula (1) that is used for treatment may increase or decrease over the course of a particular treatment period and may vary depending on the use either in a curative or preventive mode. Occasionally, repeated daily administrations of the drug, within appropriate time intervals, may be preferred.

Examples of pharmaceutically acceptable stabilizers and antioxidants include water-soluble antioxidants, such as ascorbic acid, cysteine hydrochloride, sodium metabisulfite, sodium sulfite and the like, oil-soluble antioxidants, such as ascorbyl palmitate, butylated hydroxyanisole (BHA), butylated hydroxytoluene (BHT), lecithin, propyl gallate, alpha-tocopherol, and the like, and metal chelating agents, such as citric acid, ethylenediamine tetraacetic acid (EDTA), sorbitol, tartaric acid, phosphoric acid, and the like.

Compositions of the embodiment suitable for oral administration of an effective amount are manifold and include tablets, coated tablets, dragees, hard and soft capsules, cachets, lozenges with a flavored basis containing sucrose and acacia or tragacanth, for example. Other compositions may be in the form of powders, granules, solutions, emulsions or suspensions in an aqueous or non-aqueous liquid, or as an oil-in-water or water-in-oil liquid emulsion, or as an elixir or syrup, or as pastilles using an inert base, such as gelatin and glycerin, sucrose and acacia, or enclosed in an edible coating such as propylene glycol alginate (Auguello, M. and Bliefernich, E. U.S. Pat. No. 6,699,315), each composition containing a predetermined amount of a compound of formula (1) as an active ingredient. A compound of formula (1) may also be administered as a bolus, electuary, or paste. Most preferred is the administration of the compound of formula (1) in micronized form together with an inert carrier or dispersing agent and enclosed in a gelatin capsule.

Lactose, maize starch or related materials, talc, stearic acid or its salts, and the like, can be used, for example, as carriers for tablets, coated tablets, dragees and hard gelatin capsules. Suitable carriers for soft gelatin capsules are, for example, vegetable oils, waxes, and fats, fatty acid esters, semi-solid and liquid polyols, and the like. Suitable carriers for the preparation of solutions, syrups, suspensions and nanoformulations typically employ water, polyols, carbohydrates, proteins, oil-in-water surfactants, inorganic nanoparticles, and the like.

Pharmaceutical compositions of the embodiment suitable for parenteral administration of a therapeutically effective amount comprise compounds of formula (1) in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient, or suspending or thickening agents. Such pharmaceutical compositions can also be made by forming microencapsule matrices of the compound in biodegradable polymers such as polylactide-polyglycolide. Depending on the ratio of drug to polymer, and the nature of the particular polymer employed, the rate of drug release can be controlled. Examples of other biodegradable polymers include polyorthoesters and polyanhydrides. Depot injectable formulations are also prepared by entrapping the drug in liposomes or microemulsions which are compatible with body tissue.

Suitable carriers for injection solutions or suspensions include, for example, saline, alcohols, polyols, glycerol, vegetable oils and the like. Suitable carriers for suppositories are, for example, natural or hardened oils, waxes, fats, semi-liquid or liquid polyols and the like.

Examples of suitable aqueous and nonaqueous carriers which may be employed in the pharmaceutical compositions of the embodiment include water, ethanol, polyols such as glycerol, propylene glycol, polyethylene glycol, and the like, and suitable mixtures thereof including Mygliol®, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

The pharmaceutical preparations can also contain adjuvants such as preserving agents, solubilizers, stabilizing agents, wetting agents, emulsifying agents, dispersing agents, agents, coloring agents, flavoring and sweetening agents, salts for varying the osmotic pressure, buffers, coating agents or antioxidants. Prevention of the action of microorganisms may be ensured by the inclusion of various antibacterial and antifungal agents, for example, paraben, chlorobutanol, phenol, sorbic acid, and the like. It may also be desirable to include isotonic agents, such as sugars, sodium chloride, and the like, into the compositions. In addition, they can also contain other therapeutically valuable substances.

To prolong the effect of a drug, it may be desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form and particle size in general. Alternatively, delayed absorption of a parenterally administered drug form is accomplished by dissolving or suspending the drug in an oil vehicle, for example Mygliol®. In addition, prolonged absorption of the injectable pharmaceutical form may be brought about by the inclusion of agents which delay absorption, such as gelatin, for example.

When compounds of the formula (1) are administered as pharmaceuticals to humans and animals, they can be given per se or as a pharmaceutical composition containing, for example 5 to 95% of active ingredient in combination with a pharmaceutically acceptable carrier. Regardless of the route of administration selected, the compounds of the formula (1), which may be used in a suitable hydrated form, and/or the pharmaceutical compositions of the present embodiment, are formulated into pharmaceutically acceptable dosage forms by conventional methods known to those skilled in the art.

In formula (1), $R^2$ may conveniently be 3,5-di-tert-butyl-4-hydroxyphenyl and $R^1$ may be amino. Preferred are compounds wherein $R^1$ is —$NR^3R^4$.

When $R^1$ is —$NR^3R^4$, it is preferred that $R^3$ is hydrido, methyl, trideuteromethyl, ethyl, hydroxy, methoxy, ethoxy, most preferably hydrido.

When $R^1$ is —$NR^3R^4$, it is preferred that $R^4$ is hydrido, trideuteromethyl, alkyl, halo(lower)alkyl, hydroxyl(lower) alkyl, alkylcarbonyl, alkylsulfonyl, more preferably hydrido, methyl, trideuteromethyl, ethyl, methoxy, cyclopropyl, 2-fluoroethyl, 2,2,2-trifluoroethyl, or 2-hydroxyethyl, most preferably methyl.

The compounds of formula

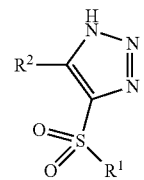

wherein the substituents $R^1$ and $R^2$ are as described above, can be prepared by different methods, one of them is exemplified in general terms in Reaction Scheme 1.

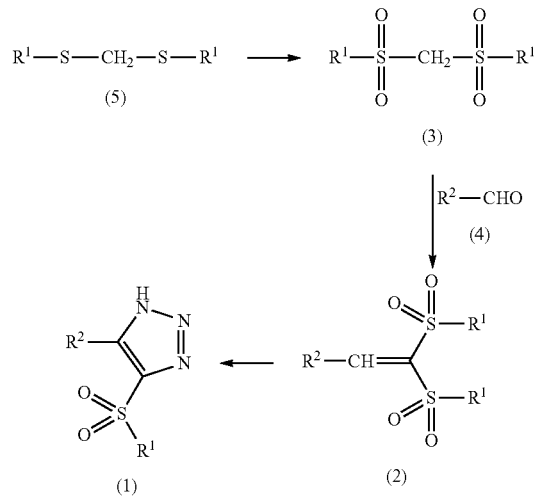

The reaction sequence commences with the dithioacetal (5), which may be commercially available or may be prepared as described in the literature, for example by Zaidi et al. (J Chem Soc Pakistan 2004, 26, 333-339) where PhSH, $CH_2O$, $CaCl_2$, and a catalytic amount of HCl was heated to reflux to obtain $(PhS)_2CH_2$, and Herriott and Picker (Synthesis 1975, 447) prepared dithioacetals by alkylation under phase-transfer conditions, e.g., PhSH, NaOH, H₂O, CH₂Cl₂, to give (PhS)₂CH₂. Compound (5) can be oxidized as described in the literature using oxidizing agents such as hydrogen peroxide, percarboxylic acids, persulfates such as Oxone, permanganates, and the like. As a further example, dimethyldioxirane, (Curi, D., et al., Heteroatom Chemistry, 1994, 5(5/6), 555-60) and perfluoro-cis-2,3-dialkyloxaziridines (DesMarteau, D. D., et al., J Org Chem 1994, 59, 2762) have more recently been described as effective reagents applicable for the oxidation of a compound of the formula (5) leading to a compound of formula (3). Of these conditions, Oxone in aqueous methanol or aqueous acetone at room temperature and a reaction time of 2-12 h is usually preferred.

The condensation reaction of the bis-sulfonylmethane of formula (3) with an aldehyde of the formula (4), leading to the addition product in the form of a bis-sulfonyl-vinyl derivative of formula (2), can be accomplished most conveniently under conventional Knoevenagel reaction conditions for an extended period, usually from hours to several days, depending on the nature of the reaction. The preferred solvent is a mixture of toluene and cyclohexane, to replace the commonly used benzene for toxicological and environmental concerns. As the base component, typically used in Knoevenagel reactions, 1-methylpiperazine is preferred. N,N-dimethylformamide or another inert, polar solvent may occasionally be added to improve solubility of the reaction partners.

Alternatively, the condensation can be conducted in acetic or propionic acid together with an inert solvent such as toluene and a base such as morpholine, piperidine, or 1-methylpiperazine. Under these conditions, reaction periods of 1 to 2 days are usually preferred. In further examples of the reaction conditions, potassium fluoride (Rand, L, et al., J Org Chem 1962, 27, 3505) and montmorillonite KSF (Bigi, F., et al., J Org Chem 1999, 64, 1033) have been propagated as catalysts. The compound of formula (3) can also be deprotonated in a separate step and then admixed with the compound of formula (4) to effect the condensation, or the reaction of compounds (3) with (4) can be conducted under phase-transfer conditions in the presence of a strong base and known to those skilled in the art.

The resulting compound of formula (2) can be isolated by precipitation, for example with hexane, or by extraction with a water-immiscible solvent such as ethyl acetate or dichloromethane. The crude product is then further purified by chromatography and/or crystallization. If acids, such as acetic or propionic acid, are used as a reaction medium, neutralization of the acid, prior to product isolation, is preferred. Alternatively, the acidic reaction mixture is diluted with water and then extracted. Neutralization of excess acid can be performed in the extract containing the condensation product.

The cyclocondensation of the compound of formula (2) can be accomplished with an azide source such as an alkali salt of hydrazoic acid, for example lithium azide or sodium azide. Similarly, tetrabutylammonium azide or the like can be employed. Of these options, sodium azide is preferred for reasons of economy. The reaction is carried out preferably in the presence of a polar organic solvent, or a suitable solvent mixture. Of these solvent, glymes and alkoxyethanols are particularly useful and methoxyethanol is preferred. The reaction temperature lays typically between 50 and 150° C., most preferred is a temperature of ca. 100° C. The resulting compound of formula (1) is recovered, for example by precipitation upon addition of water, and purified by crystallization, the crystallization step is occasionally preceded by extraction and/or flash-chromatography.

In yet another variation, the compound of formula (1) can be produced by condensing the aldehyde of formula (4) with a disulfonyl reagent, followed by the cyclocondensation with azide ion, but without prior isolation of the alkene intermediate (2) shown in Reaction Scheme 1. Previously described isolation methods can be applied to the product of formula (1). This method is particularly useful if the disulfonyl reagent of the type (3), or the intermediate (2), is of limited stability.

The method is further exemplified in Reaction Scheme 2 by the synthesis of a compound of the formula

wherein $R^1$ is methyl and $R^2$ is 3,5-di-tert-butyl-4-hydroxyphenyl as illustrated below.

Reaction Scheme 2

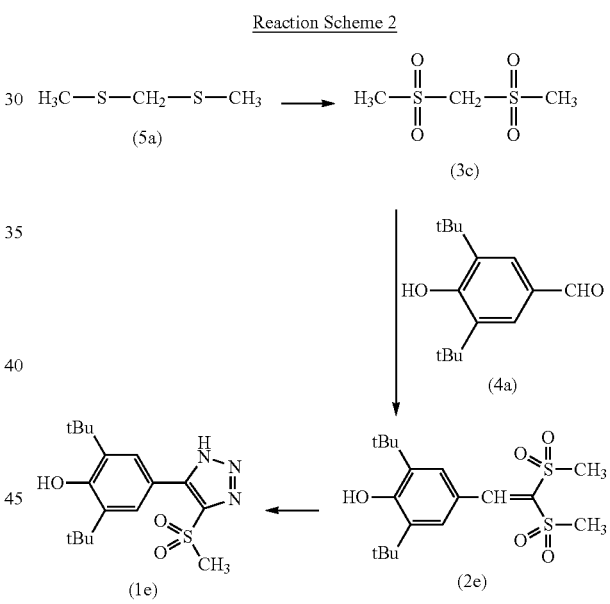

In Reaction Scheme 2, the starting materials (5a), (3c), and (4a) are known. The compound of the formula (5a) is commercially available and (3c) can be obtained from (5a) by oxidation as described in Reaction Scheme 1 wherein 30% hydrogen peroxide in acetic acid is preferred. The subsequent coupling reaction of the compound of formula (3c) with the aldehyde of the formula (4a) can be conducted as described in Reaction Scheme 1, for example by using propionic acid and toluene in various ratios. A ratio of approximately 1:1 (v/v) propionic acid—toluene as the reaction medium and N-methyl piperazine as the basic component is preferred. The reaction is typically run in a heating bath maintained at ca. 145° C. The reaction progress can be monitored most conveniently by thin-layer chromatography. The product of formula (2e) can be isolated by precipitation upon addition of water, and purified by recrystallization. A cyclocondensation of the compound of formula (2e) with sodium azide, under conditions described in connection with Reaction Scheme 1, leads to the target compound of formula (1e).

The method is further exemplified by the synthesis of a compound of the formula

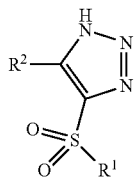

wherein $R^1$ is pheny and $R^2$ is 4-methylsulfonylphenyl, but where the substituent $R^2$ is elaborated after the cyclo condensation, as illustrated below in Reaction Scheme 3.

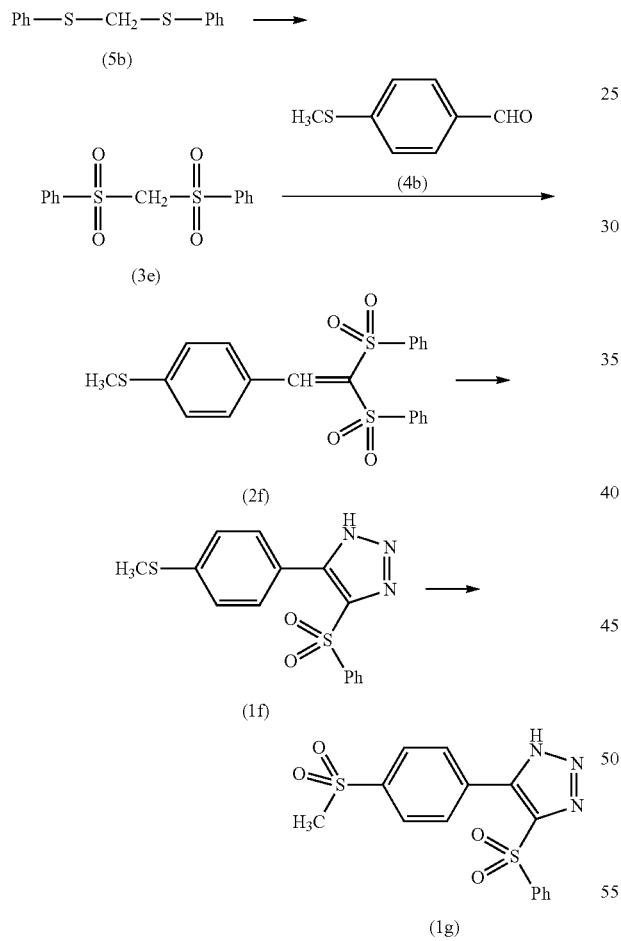

In Reaction Scheme 3, the starting materials (5b), (3e) and (4b) are known. The disulfone of formula (3e) is commercially available or can also be prepared readily from the disulfide (5b) by the oxidation procedures outlined in connection with Reaction Scheme 1. The condensation reaction between (3e) and (4b) can be conducted under the conditions previously described in connection with Reaction Scheme 2. The reaction product of formula (2f) is isolated after neutralization of the reaction mixture, extraction, evaporation of the solvents, and chromatography. The resulting compound of formula (2f) is subjected to a cyclocondensation with sodium azide as described previously and the resulting product of formula (1f) is isolated by dilution of the reaction mixture with water, filtration, and crystallization from a mixture of dichloromethane and cyclohexane. A solution of Oxone in acetone, methanol and water is the preferred reagent for the subsequent oxidation of the compound of formula (1f). The resulting compound of formula (1g) is obtained after extractive workup and crystallization.

The synthesis of a compound of the formula

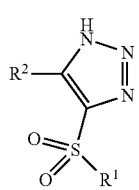

wherein $R^1$ is phenyl and $R^2$ is 3-indolyl is exemplified in Reaction Scheme 4 as illustrated below.

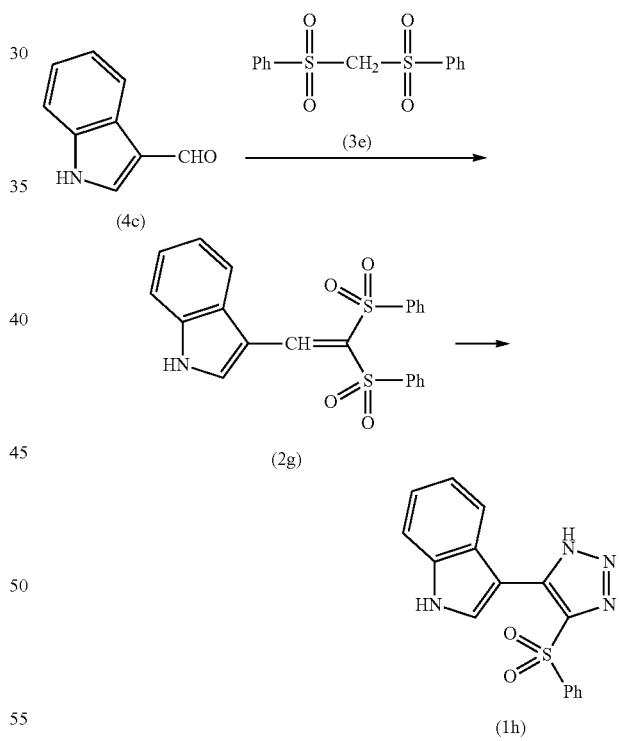

The starting material (4c) is commercially available and (3e) is obtained as described above. The condensation conditions are as described in Reaction Schemes 1 and 2. The resulting reaction mixture is equilibrated with water and a mixture of ethyl acetate and hexane, the extract is stirred with a sufficient quantity of sodium hydrogen carbonate, either as a solids or an aqueous solution, to render the aqueous layer slightly basic. The product of the formula (2g) is then isolated from the organic layer by solvent evaporation, chromatography and crystallization. A following cyclocondensation with sodium azide is conducted as described previously to yield the compound of formula (1h).

The synthesis of a compound of the formula

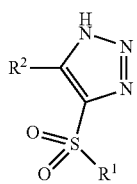

1 wherein $R^1$ and $R^2$ are as specified above can also be prepared by a method illustrated in Reaction Scheme 5 as shown below.

of sodium thiophenolate is most preferred. The preferred solvents are alcohols; of these 2-propanol is most preferred. The preferred reaction temperature is between 50 to 100° C. and the boiling point of 2-propanol is most preferred.

A following oxidation step, using conditions outlined previously, yields the compound of the formula (3a). The inequality of the groups denoted as $R^1SO_2$ and $R^5SO_2$ is carried forward to the compound of the formula (2a), which constitutes the condensation product of the disulfone of the formula (3a) and the aldehyde of the formula (4). In the subsequent cyclocondensation reaction, however, the $R^5SO_2$ group will be lost in view of the better leaving group characteristics in comparison to $R^1SO_2$. The group $R^1SO_2$ will be retained in the final product of formula (1). The relative bond

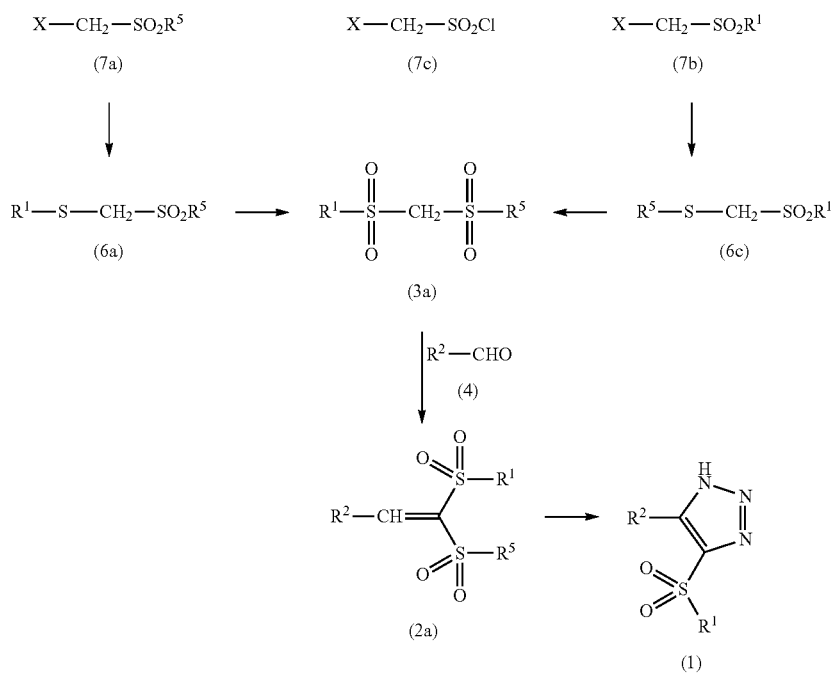

The synthesis commences with a disulfone of formula (3a) wherein the substituents $R^1$ and $R^5$ differ from each other. Such unsymmetrical disulfones of the formula (3a) can be prepared as illustrated in Reaction Scheme 5 by conveniently commencing with readily accessible starting materials of the type (7a) and (7b). A preferred example of compound (7a) is the known chloromethylsulfonylbenzene and compound (7b) can be prepared from the commercially available chloromethanesulfonyl chloride of the formula (7c) wherein X=Cl. It is known that the halogen in halomethanesulfonyl groups is difficult to displace with reagents such as amines or phenoxide ion (Johnson T. B. and Douglas, I. B., J Am Chem Soc 1941, 63, 1571). It is therefore appreciated that thiolysis reactions are more successful (U.S. Pat. No. 3,925,468, 1975). Thus, thiolysis reactions transform compounds (7a) or (7b) to the sulfanyl compounds (6a) or (6c), respectively. The preferred conditions employ an alcoholic solution of an equimolar proportion of the halomethyl compound and the thiol, in the presence of 1 to 1.2 equivalent of a strong base such as potassium tert-butoxide, at a temperature range preferable between 30 and 110° C. for a period of 30 to 120 min. Alternatively, a preformed salt of the thiol may be employed and for the construction of (6c) wherein $R^5$ is phenyl, the use strength of $R^5SO_2$ and $R^1SO_2$ in the compound of the formula (3a) can be predetermined by the proper choices of $R^5$ and $R^1$ in the compounds of formula (6a) and (6c), respectively. It will be appreciated, however, that the specific and unambiguous retention of the group $R^1SO_2$ in the triazole product (1) can be problematic if the substituents $R^1$ and $R^5$ do not differ significantly from each other.

The concept of the synthetic approach using different groups for $R^1$ and $R^5$, with the predetermined retention of $R^1$ in the final triazole product, is illustrated in Reaction Scheme 6 for the preparation of a compound of the formula

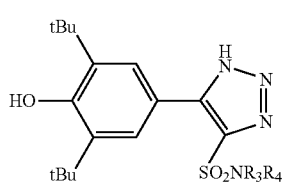

1b wherein the substituents $R^3$ and $R^4$ are as defined previously.

Reaction Scheme 6

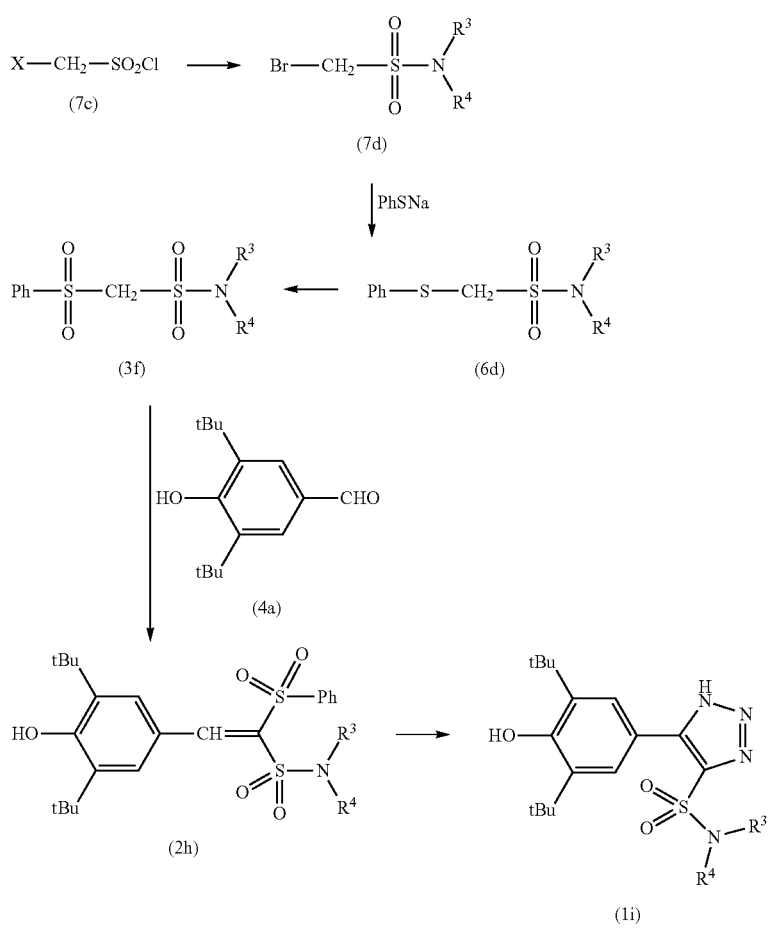

The central intermediate of formula (3f) is designed to feature $SO_2NR^3R^4$ as the group with the stronger bond toward the central methylene group. The phenylsulfonyl group assumes the role of $R^5SO_2$ with the intent to be lost in the cyclocondensation step.

The reaction sequence commences with a halomethanesulfonyl halide, such as bromomethanesulfonyl chloride, or the commercially available chloromethanesulfonyl chloride. Compound (7c), wherein X=Br, can be prepared as described (FR 2576021, 1986) from dibromomethane and sodium sulfite at elevated temperature. The resulting sodium salt is then treated with phosphorus pentachloride to furnish bromomethanesulfonyl chloride. The following reaction with the amine component can be carried out by adding a solution of halomethanesulfonyl chloride to a solution of the amine component. It is usually more convenient to add a solution of the amine component to a solution of the halomethanesulfonyl chloride. A wide range of solvents and temperatures are compatible with this reaction. Temperatures ranging from −20 to 25° C. and solvents of low to medium polarity such acetonitrile and tetrahydrofuran are preferred. Occasionally a two phase system consisting of dichloromethane and water is preferred. The resulting compound of formula (6d) is oxidized to give compound (3f) by methods previously described.

A condensation of compound (3f) with the aldehyde (4a) yields compound (2h) and a subsequent cyclocondensation reaction furnishes product (1i) as depicted in Reaction Scheme 6 by employing procedures previously described. The final product of the formula (1i) is isolated by precipitation and crystallization.

The synthesis of a compound of the formula

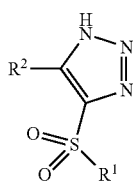

1 wherein $R^1$ and $R^2$ are as specified above can further be prepared by a method illustrated in Reaction Scheme 7 and shown below.

Reaction Scheme 7

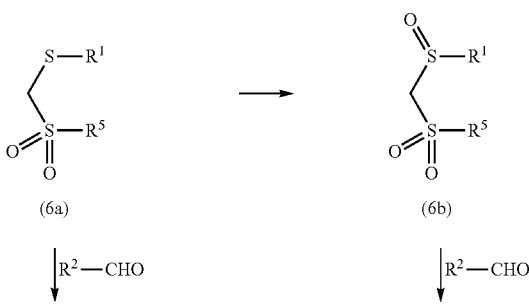

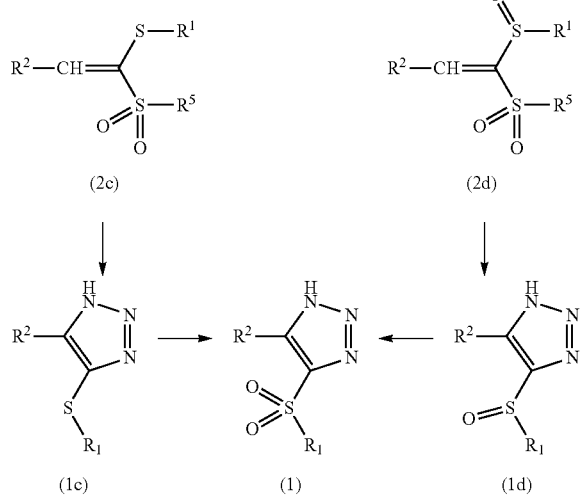

(2c)    (2d)

(1c)    (1)    (1d)

The purpose of these reaction sequences is the enhancement of the difference between groups comprising $R^1$ and $R^5$ in terms of their leaving aptitudes in the cyclocondensation steps. In accordance with this embodiment, compounds (2c) and (2d) are converted to compounds (1c) and (1d), respectively, by employing reaction conditions described previously. Since alkyl and aryl sulfides and their sulfinyl analogs are poorer leaving groups in comparison with the corresponding sulfonyl analogs, the retentions of those functionalities in the products of the formulas (1c) and (1d) are enforced. Either of these two groups can be converted to the sulfone stage by methods described previously and leading to the compound of formula (1).

The compounds of formula (6a) and (6b) can be employed directly in the Knoevenagel-type reactions with the aldehyde of formula (4) leading to the compound of formulas (2c) and (2d), respectively. The corresponding procedures were previously described. To prepare the compound of formula (6b) it is required that the divalent sulfur functionality in (6a) is selectively oxidized to the sulfinyl stage. This oxidation, preferably performed with sodium metaperiodate or one equivalent of m-chloroperbenzoic acid in dichloromethane as described (Russel, G. A. and Ochrymowycz, L. A., J Org Chem 1970, 35, 2106), yields the compound of formula (6b). The condensation of the compounds of formulas (6a) and (6b) with the aldehyde of formula (4) can be conducted by methods previously described.

Especially preferred compounds of formula (1) are:
4-[4-(benzenesulfonyl)-1H-triazol-5-yl]-2,6-di-tert-butylphenol,
2,6-di-tert-butyl-4-[4-(2-hydroxyethylsulfonyl)-1H-triazol-5-yl]phenol,
5-(3,5-di-tert-butyl-4-hydroxy-phenyl)-N-hydroxy-N-methyl-1H-triazole-4-sulfonamide,
N-cyclopropyl-5-(3,5-di-tert-butyl-4-hydroxy-phenyl)-1H-triazole-4-sulfonamide,
2,6-di-tert-butyl-4-[4-(2-fluoroethylsulfonyl)-1H-triazol-5-yl]phenol,
5-(3,5-di-tert-butyl-4-hydroxy-phenyl)-N-(2,2,2-trifluoroethyl)-1H-triazole-4-sulfonamide,
5-(3,5-di-tert-butyl-4-hydroxy-phenyl)-N-methoxy-1H-triazole-4-sulfonamide,
2,6-di-tert-butyl-4-(4-methylsulfonyl-1H-triazol-5-yl)phenol,
5-(3,5-di-tert-butyl-4-hydroxy-phenyl)-1H-triazole-4-sulfonamide,
5-(3,5-di-tert-butyl-4-hydroxy-phenyl)-N-methyl-1H-triazole-4-sulfonamide,
3-[4-(benzenesulfonyl)-1H-triazol-5-yl]-1H-indole,
5-(3,5-di-tert-butyl-4-hydroxy-phenyl)-N-ethyl-1H-triazole-4-sulfonamide, and
4-(benzenesulfonyl)-5-(4-methylsulfonylphenyl)-1H-triazole.

As mentioned earlier, the compounds of formula (1) and pharmaceutically acceptable salts of compounds of formula (1) are useful in the treatment or prevention of inflammations. For example, they can be used as anti-inflammatory agents in the treatment of inflammatory joint diseases, such as arthritis, and in other diseases where inflammation is the inherent cause. To demonstrate their utility, compounds of formula (1) were tested for their inflammation-inhibiting properties in the adjuvant-induced arthritis test in rats as described in Int J Immunopharma 1990, 12, 709-712, and exemplified by a representative compound of formula (1) described above.

The adjuvant was prepared by homogenizing 170 mg of heat-killed and dried *mycobacterium tuberculosis* (Difco) in 22.7 mL of 'Incomplete Freund's Adjuvant' (ICFA, Difco). Male Lewis rats with body weights of 130-150 g were injected i.d. at the base of the tail with 0.1 ml of adjuvant. The non-diseased animals received 0.1 mL of ICFA i.d. The animals were housed individually and received feed and water ad libitum. The thus-induced arthritis was allowed to develop without treatment during 21 days. On day 21 the body weight of each animal was determined. At the same time, the volumes of the two hind paws of each animal were measured by immersing the paws in an aqueous plethysmograph up to the height of the lateral malleolus. Thereupon, the animals were divided into groups, each group comprising six animals of approximately the same average volumes of the left hind paws. One group was administered the drug vehicle. The drug-vehicle was prepared by dissolving 2.5 g of carboxymethylcellulose, 4.5 g of sodium chloride, 2 mL of Tween-80 and 4.5 mL of benzyl alcohol in 500 mL of water. The other groups were administered the test compounds, homogeneously suspended in the vehicle, by intubation each day over a period of seven days. Paw volumes and body weight were recorded diurnally. At the end of the treatment period (day 28), body weights and volumes of the hind paws were again determined. The changes over the treatment period were calculated. The change in paw volume or body weight equals the paw volume or body weight on day 28 minus paw volume or body weight on day 21. Subsequently, the animals were sacrificed and the liver weights recorded. The results determined for a representative compound of formula (1) in the test described hereinbefore, after 7 treatment days at a dose level of 30 mg/kg, are set forth in the following Table I. The standard deviations are listed in parentheses.

TABLE 1

| | Volume change of left paw (mL) | Volume change of right paw (mL) | Change of body weight (g) | Liver weight on day 8 (g) |
|---|---|---|---|---|
| Vehicle (Non-diseased) | +0.03 (0.002) | +0.13 (0.01) | +17 (1.4) | 11.54 (0.59) |
| Compound 1i | −0.73 (0.08) | −0.63 (0.11) | +21 (1.4) | 8.80 (0.63) |
| Vehicle (Diseased) | +0.28 (0.04) | +0.34 (0.04) | +15 (1.2) | 8.71 (1.20) |

Compound 1i (Scheme 6, $R^3$ = H, $R^4$ = CH$_3$) is micronized 5-(3,5-di-tert-butyl-4-hydroxy-phenyl)-N-methyl-1H-triazole-4-sulfonamide.

The representative compound of formula (1i wherein $R^3$=H, $R^4$=CH$_3$), was also tested for the effects on the activity of purified COX-1 and COX-2 enzymes. In sharp contrast to the potent activity in the adjuvant-induced arthritis test in rats, the activity against the isolated arachidonic acid metabolizing enzymes was relatively low.

COX activity was measured using an assay kit obtained from Cayman Chemicals in accord with the instruction manual of the manufacturer "COX Activity Assay, Catalog No. 760151, Colorimetric Assay for the Determination of COX Activity." The enzyme activity was determined by the peroxidase activity of cyclooxygenases on arachidonic acid and monitored colorimetrically at 590 nm by the appearance of oxidized N,N,N',N'-tetramethyl-p-phenylenediamine. Both ovine COX-1 and human recombinant COX-2 were obtained from Cayman Chemicals. At a level of 300 µM, the test substance (formula II wherein $R^3$=H, $R^4$=$CH_3$) showed no effect on COX-1 and the $IC_{50}$ for COX-2 was 68 µM.

The compounds of formula (1) can be used as medicaments, most appropriately in the form of pharmaceutical preparations. The pharmaceutical preparations can be administered orally, or parenterally, for example in the form of suppositories, as solutions or suspensions for injection, or transdermally.

For the preparation of pharmaceutical dosage forms, the compounds of formula (1) and their pharmaceutically acceptable addition salts can be processed with pharmaceutically established inorganic or organic carriers employing the drug substance in the form of micronized crystals, co-precipitated amorphous material, or as micronized amorphous drug substance. The overarching goal consists in enhancing solubility of the active pharmaceutical ingredient, to promote drug penetration and permeation and to achieve these goals in a form that is most beneficial for the subject.

The present embodiment is illustrated below with the aid of examples. These illustrations are given solely by way of examples and are not intended to limit the general spirit and scope of the embodiment.

Example 1

4-[2,2-bis(methylsulfonyl)vinyl]-2,6-di-tert-butyl-phenol

Compound 2e, Scheme 2

Bis(methylsulfanyl)methane was oxidized as described (Justus Liebig Annalen der Chemie 1965, 685, 29-35) using a solution of hydrogen peroxide in acetic acid to give bis(methylsulfonyl)methane, mp 146° C. A round bottom flask equipped with a toluene-filled Dean Stark trap and magnetic stirrer was charged with 3,5-di-tert-butyl-4-hydroxy-benzaldehyde hemihydrate (0.49 g, 2 mmol) and bis(methylsulfonyl)methane (0.38 g, 2.2 mmol), propionic acid (6 mL) and toluene (4 mL). To this mixture was added N-methyl piperazine (0.14 g) and the flask was stirred and immersed into a bath maintained at 145° C. for a period of 52 h. The solution was allowed to cool to room temperature and was then poured into a beaker with ethyl acetate (50 mL) and saturated sodium hydrogen carbonate solution (25 mL). This mixture was stirred and solid sodium hydrogen carbonate (7 g) was added in portions. The aqueous layer was re-extracted with ethyl acetate (30 mL) and the combined organic layers were washed with saturated sodium hydrogen carbonate solution (25 mL), brine (5 mL), then dried (sodium sulfate) and evaporated to brown syrup. This material was chromatographed on a silica gel column using 1:1:6 ethyl acetate-dichloromethane-hexane as mobile phase. Residual starting material was eluted first and was followed by the product that crystallized in the column effluent. The fractions containing the product were pooled and evaporated and the resulting residue (0.49 g) was recrystallized from dichloromethane—cyclohexane to afford the title compound as white needles, 0.30 g, mp 208-9° C., TLC (1:1 ethyl acetate—hexane, Rf 0.24), $^1$H-NMR (300 MHz, $CDCl_3$) δ 1.47 (9H, s), 3.30 (3H, s), 3.38 (3H, s), 5.92, (1H, s), 7.80 (2H, s), 8.27 (1H, s).

Example 2

2,6-di-tert-butyl-4-(4-methylsulfonyl-1H-triazol-5-yl)phenol

Compound 1e, Scheme 2

A round-bottom flask was charged with 4-[2,2-bis(methylsulfonyl)vinyl]-2,6-di-tert-butyl-phenol (0.292 g, 0.752 mmol), sodium azide (80 mg, 1.23 mmol) and 2-methoxyethanol (2 mL). The mixture was stirred and immersed into a heating bath maintained at 105-110° C. for 20 min. During this period the starting material (TLC, 1:2 ethyl acetate—hexane, Rf 0.66; TLC, 1:19 methanol—dichloromethane, Rf 0.95) was consumed. The stirred solution was allowed to cool, and then diluted by the dropwise addition of water until turbidity was reached. Stirring was continued until crystallization commenced. Additional water was then added and the white crystalline suspension was stirred for 30 min and then refrigerated. The solids were filtered off, washed with water, and dried. This material was recrystallized from ethanol—water, the resulting suspension was filtered and the solids washed with water and dried to constant weight at 60° C., to yield the title compound as a white material, 0.175 g; TLC, 1:2 ethyl acetate—hexane, Rf 0.18; TLC, 1:19 methanol—dichloromethane, Rf 0.39; $^1$H-NMR (300 MHz, $CDCl_3$) δ 1.47 (9H, s), 3.33 (3H, s), 5.53 (1H, s), 7.70 (2H, s).

Example 3

1-Bromo-N-methyl-methanesulfonamide

Compound 7d, $R^3$=H, $R^4$=$CH_3$, Scheme 6

A 125-mL 3-neck round-bottom flask, equipped with magnetic stirrer and thermometer was charged with the known bromo-methanesulfonyl chloride (formula 7c, 5.00 g, 25.8 mmol) and dichloromethane (25 mL). The solution was cooled to −10° C., stirred vigorously, and an aqueous 40% methylamine solution (4.64 mL, 56.9 mmol) was added, at a rate so that the temperature of the mixture did not exceed 0° C. Within the next 60 min the temperature was allowed to gradually reach 15° C. The mixture was stirred for an additional 15 min at 15° C. and diluted with water (10 mL). The aqueous layer was extracted with dichloromethane (8 mL), the combined dichloromethane layers were washed with saturated aqueous sodium hydrogen carbonate solution, dried (sodium sulfate) and concentrated. The resulting crystalline suspension was diluted with hexane and refrigerated overnight; the mother liquor was decanted off to leave the title compound as light tan crystals, 3.55 g; TLC (1:1 ethyl acetate—hexane, Rf 0.57, detection with iodine); $^1$H-NMR (300 MHz, DMSO-$d_6$) δ 2.60 (3H, d), 4.84 (2H, s), 7.50 (1H, br s).

Example 4

N-methyl-1-phenylsulfanyl-methanesulfonamide

Compound 6d, $R^3$=H, $R^4$=$CH_3$, Scheme 6

A 25-mL round bottom flask was charged with N-methyl-bromomethanesulfonamide (1.88 g, 10 mmol), sodium thiophenolate (1.38 g, 10.4 mmol), and 2-propanol (15 mL). The mixture was immersed into a bath maintained at 90° C. and stirred for 75 min. The resulting suspension was evaporated, the residue was distributed between ethyl acetate (40 mL) and water (20 mL) and the aqueous layer was re-extracted once with ethyl acetate (15 mL). The combined organic layers were washed with water (10 mL) and brine (5 mL), dried (sodium sulfate) and evaporated. A flash chromatogram using 1:1 ethyl acetate—hexane as mobile phase eluted residual thiophenol (TLC, silica gel, 1:1 ethyl acetate—hexane, Rf 0.90). The title compound was eluted subsequently and obtained as a colorless oil after evaporation of the solvent, 1.52 g; TLC (1:1 ethyl acetate—hexane) Rf 0.63, $^1$H-NMR (300 MHz, CDCl$_3$) δ 2.66 (3H, d, J=5 Hz), 4.29 (2H, s), 4.34 (1H, br s), 7.36 (3H, m), 7.59 (2H, m).

Example 5

1-(benzenesulfonyl)-N-methyl-methanesulfonamide

Compound 3f, $R^3$=H, $R^4$=CH$_3$, Scheme 6

A stirred solution of N-methyl-1-phenylsulfanyl-methanesulfonamide (5.43 g, 25 mmol) in methanol (100 mL) was cooled in an ice bath and a solution of Oxone (23 g) in water (100 mL) was added. The ice bath was removed after 5 min and stirring continued for 14 h at room temperature. The suspension was concentrated under reduced pressure to a weight of 62 g and then diluted with water to a weight of 100 g. This crystalline suspension was filtered, the filter cake washed with water and dried to afford the title compound, 3.64 g, mp 116° C. After recrystallization from methanol-water, mp 118-9° C.; TLC (1:1 ethyl acetate—hexane) Rf 0.34; $^1$H-NMR (300 MHz, CDCl$_3$) δ 2.92 (3H, d, J=5.4 Hz), 4.58 (2H, s), 5.10 (1H, br s), 7.61 (2H, t, J=8 Hz), 7.73 (1H, dd, J=8 and 8 Hz), 7.98 (2H, d, J=8 Hz).

Example 6

1-(Benzenesulfonyl)-2-(3,5-di-tert-butyl-4-hydroxy-phenyl)-N-methyl-ethenesulfonamide Compound 2h, $R^3$=H, $R^4$=CH$_3$, Scheme 6

A round bottom flask equipped with a toluene-filled Dean Stark trap and magnetic stirrer was charged with 1-(benzenesulfonyl)-N-methyl-methanesulfonamide (1.73 g, 6.9 mmol), 4-hydroxy-3,5-di-t-butyl-benzaldehyde hemihydrate (compound 4a, 1.75 g, 7.2 mmol), propionic acid (21 mL), toluene (14 mL) and 1-methylpiperazine (0.5 g). The flask was stirred and immersed into a bath maintained at 145° C. for a period of 18 h. The dark solution was allowed to cool to room temperature and was then equilibrated with ethyl acetate (200 mL) and water (100 mL). The organic layer was washed with water (150 mL), twice with saturated sodium hydrogen carbonate solution (100 mL each) and then evaporated. The residue was chromatographed on a silica gel column using 1:1 dichloromethane—hexane to elute a brown material. The mobile phase was changed to 1:4 ethyl acetate—hexane eluting the title compound as a nearly equal mixture of two geometric isomers, 1.23 g; TLC (1:4 ethyl acetate—hexane) Rf 0.22; $^1$H-NMR (300 MHz, CDCl$_3$) δ 1.41 (9H, s), 1.48 (9H, s), 2.63 (3H, d), 2.88 (3H, d), 5.07 (1H, m), 5.35 (1H, m), 6.80 (1H, s), 6.85 (1H, s), 7.42 (2H, m), 7.50-7.64 (4H, m), 7.61 (1H, s), 7.82 (1H, s), 7.95 (4H, m), 8.25 (1H, s), 8.45 (1H, s). This mixture was used directly in the next step.

Example 7

5-(3,5-di-tert-butyl-4-hydroxy-phenyl)-N-methyl-1H-triazole-4-sulfonamide

Compound 1i, $R^3$=H, $R^4$=CH$_3$, Scheme 6

A 25-mL round-bottom flask was charged with 1-(benzenesulfonyl)-2-(3,5-di-tert-butyl-4-hydroxy-phenyl)-N-methyl-ethenesulfonamide (0.97 g, 2.08 mmol), 2-methoxyethanol (5 mL), and sodium azide (70 mg, 2.6 mmol). The mixture was stirred and immersed into a bath maintained at 105-110° C. for 80 min. Progress of the reaction was monitored by the disappearance of the starting material (TLC, 1:1 ethyl acetate—hexane, Rf 0.80) and generation of the product (Rf 0.47, elongated spot). The tan solution was gradually diluted with drops of water to precipitate the product as a sticky solid. This mixture was refrigerated for several h, the supernatant liquid was decanted and the tan solids dried at 60° C. and 20 torr. The resulting residue was dissolved in little dichloromethane, diluted with 1:3 ethyl acetate—hexane and then flash-chromatographed using 1:3 ethyl acetate—hexane as mobile phase. Dark colored impurities preceded the product band which was evaporated. The residue was taken up in ethyl acetate, filtered and evaporated again then crystallized from dichloromethane—cyclohexane. The resulting eggshell colored solids were filtered off, washed with cyclohexane and pentane, then recrystallized from ethyl acetate—cyclohexane. This material was dissolved in methanol and water added in small increments to give crystals which were washed with a small amount of 40% methanol then with water and dried at 70° C. and 25 torr for 48 h to give the title compound, 0.3221 g; $^1$H-NMR (300 MHz, CDCl$_3$) δ 1.48 (9H, s), 2.87 (3H, d, J=5 Hz), 4.90 (1H, br s), 5.52 (1H, s), 7.69 (2H, s), 11.9 (1H, br s).

Example 8

Chloromethanesulfonamide

Compound 7b, X=Cl, $R^1$=NH$_2$, Scheme 5

A 100-mL 3-neck round-bottom flask, equipped with magnetic stirrer and thermometer, was charged with the commercially available chloromethanesulfonyl chloride (ca. 90% purity, 5.13 g (31 mmol) and 1:1 ether—dichloromethane (60 mL). This solution was cooled to −10° C. and ammonia gas was introduced for 10 min to form a white suspension. This mixture was allowed to reach room temperature; the suspension was filtered through Celite, the filter cake washed with dichloromethane, then re-suspended in dichloromethane and filtered again, to yield the title compound from the filtrate as crude, white solids, 4 g. This material was used directly in the next step.

Example 9

Benzenesulfonylmethanesulfonamide

Compound 3a, $R^1$=NH$_2$, $R^5$=phenyl, Scheme 5

A round-bottom flask was charged with the crude chloromethanesulfonamide obtained as described above (4 g). To this material was added a mixture comprising water (10 mL), sodium hydroxide 1.65 g (41.25 mmol) and benzenethiol (3.64 g, 3.39 mL, 33 mmol). Additional water (19 mL) was used to rinse the benzene thiolate solution into the flask. The stirred mixture was immersed into a heating bath maintained at 115° C. for 1 h and then allowed to cool overnight. The resulting crystalline suspension was filtered; the filter cake was washed with ice-cold water then dried to constant weight to yield crude phenylsulfanylmethanesulfonamide (Scheme 5, compound 6a, $R^1$=phenyl, $R^5$=$NH_2$, 3.61 g).

The crude phenylsulfanylmethanesulfonamide (3.54 g, 17.4 mmol) obtained as described above was dissolved in acetone (75 mL) and a solution of Oxone (16 g, 52 mmol peroxysulfate) in water (75 mL) was added. The white suspension was stirred for 4 h then concentrated under reduced pressure to remove most acetone. The resulting suspension was filtered and the solids washed with ice-cold water, dried over potassium hydroxide at 25 torr and 65° C. overnight, 3.42 g. This material was not homogeneous as judged by TLC (1:1 ethyl acetate—hexane) and was suspended in acetic acid (20 mL). To this suspension was added 30% hydrogen peroxide (8 mL). The mixture was stirred overnight, heated at reflux temperature for one hour, cooled to room temperature, and diluted with water. The resulting suspension was filtered; the filter cake was washed with ice-cold water, dried over potassium hydroxide at 25 torr and 65° C. to constant weight, to afford the title compound, 2.77 g; mp 196° C.; $^1$H-NMR (300 MHz, DMSO-$d_6$) δ 5.18 (2H, s), 7.39 (2H, s), 7.65 (2H, m), 7.75 (1H, m), 7.96 (2H, m).

Example 10

5-(3,5-Di-tert-butyl-4-hydroxy-phenyl)-1H-triazole-4-sulfonamide

Compound 1i, $R^3$=$R^4$=H, Scheme 6

A round bottom flask equipped with magnetic stirrer, Dean-Stark trap, nitrogen sweep, and reflux condenser was charged with benzenesulfonylmethanesulfonamide (1.05 g, 4.46 mmol), 4-hydroxy-3,5-di-t-butyl-benzaldehyde hemihydrate (compound 4a, 1.17 g, 4.80 mmol), 2-methoxyethanol (18 mL), toluene (9 mL), and morpholine acetate (0.7 g). The trap was filled with toluene and the stirred flask was immersed into a heating bath, maintained at 135° C., for a period of 19 h. The toluene was distilled off, the bath temperature was reduced to 100° C. and sodium azide (0.52 g, 8 mmol) was added. The mixture was stirred in the heating bath for 2 h, allowed to cool to room temperature and then equilibrated with water (30 mL) containing ca. 3 mL of brine and ethyl acetate (60 mL). The organic layer was washed with water containing a small amount of brine (15 mL) and then with 1:1 brine—water (10 mL), dried and evaporated to a brown oil. This material crystallized to afford a brown mass. This residue was taken up in dichloromethane, some insoluble crystalline matter was removed by filtration and the filtrate was chromatographed on silica gel. Some colored impurities were eluted with dichloromethane. The mobile phase was changed to 1:4 ethyl acetate—hexane to elute additional colored matter. The mobile phase was then changed to 1:2 ethyl acetate—hexane which eluted the product. The fractions containing the product were pooled and evaporated. The residue was taken up in a minimum quantity of ethyl acetate, the solution was diluted with little cyclohexane and filtered through a shallow bed of Celite. The filtrate was concentration to small volume, diluted with cyclohexane and allowed to crystallize at room temperature. The solids were recrystallized from ethyl acetate—cyclohexane. The resulting suspension was filtered and the solids were washed with cyclohexane and dried, 0.85 g. This material was recrystallized again from ethyl acetate—cyclohexane and the solids were washed with cyclohexane and then with pentane (0.72 g). This material was redissolved in methanol, filtered, concentrated, and then diluted with water whereupon it crystallized in prisms. This suspension was refrigerated and the solids were filtered off. These crystalline solids were washed with water, dried for 2 d at room temperature then at 70° C. and 25 torr for 6 h, to afford the title compound, 0.70 g; $^1$H-NMR (500 MHz, DMSO-$d_6$) δ 1.40, (9H, s), 7.32 (1H, s), 7.66 (2H, s), 7.73 (2H, s).

Example 11

3-[2,2-bis(benzenesulfonyl)vinyl]-1H-indole

Compound 2g, Scheme 4

A round bottom flask equipped with magnetic stirrer, Dean-Stark trap, nitrogen sweep, and reflux condenser was charged with benzenesulfonylmethylsulfonylbenzene (0.290 g, 2 mmol, TLC, 1:1 ethyl acetate—hexane, Rf 0.60), 1H-indole-3-carbaldehyde (0.290 g, 2 mmol), propionic acid (5 mL), toluene (5 mL), and N-methyl piperazine (0.14 g). The stirred mixture was immersed into a heating bath maintained at 145° C. for a period of 18 h. The mixture was allowed to cool and was then equilibrated with 1:1 ethyl acetate—hexane (35 mL) and water (20 mL). The organic layer was washed with water (20 mL) saturated sodium hydrogen carbonate solution (25 mL) and brine (5 mL). The solution was dried (sodium sulfate) and evaporated to give a brown syrup which solidified. This material (0.85 g) was dissolved in dichloromethane and chromatographed on silica gel using 1:1 dichloromethane hexane as mobile phase. The solvent mixture was changes to 4:1:5 dichloromethane—ethyl acetate—hexane eluting small amounts of unreacted benzenesulfonylmethylsulfonylbenzene (TLC, 1:1 ethyl acetate—hexane, Rf 0.60), followed by the product (TLC, 1:1 ethyl acetate—hexane, Rf 0.49), and then by unreacted 1H-indole-3-carbaldehyde (TLC, 1:1 ethyl acetate—hexane, Rf 0.32). The fractions containing the product were pooled and evaporated, the resulting residue was recrystallized from dichloromethane—hexane, the crystals were washed with pentane to afford the title compound as tan needles, 0.42 g; $^1$H-NMR (300 MHz, CDCl$_3$) δ 7.34 (3H, m), 7.37-7.49 (3H, m), 7.49-7.64 (3H, m), 7.87 (1H, m), 8.03 (4H, m), 8.88 (1H, d, J=5 Hz), 8.98 (1H, s), 9.00 (1H, br).

Example 12

3-[4-(benzenesulfonyl)-1H-triazol-5-yl]-1H-indole

Compound 1h, Scheme 4

A flask equipped with a magnetic stirrer and reflux condenser with nitrogen sweep was charged with 3-[2,2-bis(benzenesulfonyl)vinyl]-1H-indole (0.41 g, 0.968 mmol), sodium azide (0.1 g, 1.5 mmol) and 2-methoxyethanol (3 mL). The mixture stirred and immersed into a heating bath maintained at 105-110° C. for a period of 3 h. The solution was allowed to reach room temperature and was then equilibrated with ethyl acetate (15 mL). The organic layer was washed twice with water (5 mL), once with brine (5 mL) then dried (sodium sulfate) and evaporated. The residual oily residue was partially suspended in 1:4 ethyl acetate—hexane and enough dichloromethane was then added to make a solution which caused crystallization. Additional hexane was added; the suspension was heated to remove some dichloromethane, then allowed to cool, first at room temperature and then in the refrigerator overnight. The mother liquor was decanted and the residual brown crystals were washed with pentane (0.23 g). This material was decolorized by a passage through a silica gel column using 1:3→1:2→1:1 ethyl acetate—hexane as stepwise gradient. The resulting crystalline residue was dissolved in methyl acetate and cyclohexane was added, then concentrated, diluted with little dichloromethane, heated to reflux, and ethyl acetate was added. The resulting solution was concentrated, diluted with cyclohexane, and allowed to crystallize in the refrigerator. The mother liquor was decanted and the solids were washed with 1:1 dichloromethane—hexane, then with pentane, to yield the title compound as light straw-colored solids, 0.204 g; TLC (1:1, ethyl acetate—hexane) Rf 0.44; mp 109-110° C.; $^1$H-NMR (500 MHz, DMSO-$d_6$) δ 7.12 (1H, t, J=7.5), 7.21 (1H, t, J=7.5 Hz), 7.5 (1H, d, J=7.5 Hz), 7.59 (2H, dd, J=7 and 7.5 Hz), 7.69 (1H, t, J=7 Hz), 7.89 (2H, d, J=7.5 Hz), 8.09 (1H, br), 11.71 (1H, br), 15.97 (1H, br).

Example 13

1-[2,2-bis(benzenesulfonyl)vinyl]-4-methylsulfanyl-benzene

Compound 2f, Scheme 3

A round bottom flask equipped with magnetic stirrer, Dean-Stark trap, nitrogen sweep, and reflux condenser was charged with benzenesulfonylmethylsulfonylbenzene (0.5927 g, 2 mmol), 4-methylsulfanylbenzaldehyde (0.3044 g, 2 mmol), propionic acid (6 mL), toluene (4 mL), and N-methyl piperazine (0.14 g). The stirred mixture was immersed into a heating bath maintained at 145° C. for 14 h. The mixture was allowed to cool and was then equilibrated with 1:1 ethyl acetate—hexane (35 mL) and water (20 mL). The organic layer was washed with water (20 mL) and then with saturated sodium hydrogen carbonate solution (ca. 25 mL). The weakly basic aqueous layer was discarded and the organic layer was washed with brine (5 mL), dried and evaporated to a brown syrup which solidified on standing. This material was chromatographed using 1:6 ethyl acetate—hexane as mobile phase with a sufficient quantity of dichloromethane to dissolve the sample. A very dark band was eluted in the first fraction. Chromatography was continued with 1:4 and 1:2 ethyl acetate—hexane separating the product with Rf 0.53 from unreacted aldehyde, Rf 0.80, and disulfone, Rf 0.33 (TLC 1:2 ethyl acetate—hexane). The fractions containing the product were pooled, together with the material that had crystallized in the receptacles. The mixture was evaporated and the residue was recrystallized from dichloromethane—hexane to afford the title compound, 0.17 g; mp 170° C., $^1$H-NMR (300 MHz, CDCl$_3$) δ 2.52 (3H, s), 7.20 (2H, m), 7.38 (2H, m), 7.50-7.69 (6H, m), 7.78 (2H, m), 8.03 (2H, m), 8.56 (1H, s).

Example 14

4-(benzenesulfonyl)-5-(4-methylsulfanylphenyl)-1H-triazole

Compound 1f, Scheme 3

A round bottom flask equipped with a magnetic stirrer and reflux condenser with nitrogen sweep was charged with 1-[2,2-bis(benzenesulfonyl)vinyl]-4-methylsulfanyl-benzene (0.2714 g, 0.63 mmol), sodium azide (65 mg, 1 mmol) and 2-methoxyethanol (2 mL). The mixture was stirred and immersed into a heating bath maintained at 105-110° C. for a period of 20 min. The stirred solution was allowed to reach room temperature and water (ca. 6 mL) was added dropwise to form a precipitate. This ochre suspension was stirred overnight and then filtered; the filter cake was washed exhaustively with water and then dried. The residue was taken up in dichloromethane, the solution was filtered, the filtrate was diluted with cyclohexane and concentrated to give a crystalline deposit (0.18 g) which was dissolved in little acetone and diluted with water to turbidity to induce crystallization. The crystals were isolated by decantation of the mother liquor and dried to afford the title compound (0.1752 g); mp 148° C.; TLC (ethyl acetate) Rf 0.67, streaky. This material was used directly in the next step.

Example 15

4-(benzenesulfonyl)-5-(4-methylsulfonylphenyl)-1H-triazole

Compound 1g, Scheme 3

A round bottom flask was charged with 4-(benzenesulfonyl)-5-(4-methylsulfanylphenyl)-1H-triazole (0.1657 g, 0.50 mmol) as obtained above. This material was dissolved in a mixture of methanol (2 mL) and acetone (0.5 mL) and a solution of Oxone (0.461 g, 1.5 mmol persulfate) dissolved in water (2.5 mL) was added. The mixture was stirred for 24 h, partially evaporated, then diluted with water. The resulting suspension was filtered, the filter cake was washed with water, re-suspended in water and filtered again and dried to yield the title compound as a light straw-colored powder (0.17 g); $^1$H-NMR (500 MHz, DMSO-$d_6$) δ 3.30 (3H, s), 7.64 (2H, t, J=7.5 Hz), 7.76 (1H, t, J=7.5 Hz), 7.92 (2H, d, J=7.5 Hz), 8.00 (2H, d, J=8.5 Hz), 8.09 (2H, d, J=8.5 Hz).

Example 16

| Tablet Formulation (Wet Granulation) | | | | | |
|---|---|---|---|---|---|
| Item | Ingredients | mg/tablet | | | |
| 1 | Compound 1i (R$^3$ = H, R$^4$ = CH$_3$) | 25 | 100 | 250 | 500 |
| 2 | Anhydrous Lactose | 83 | 35 | 19 | 38 |
| 3 | Croscarmellose Sodium | 6 | 8 | 16 | 32 |
| 4 | Povidone K30 | 5 | 6 | 12 | 24 |
| 5 | Magnesium stearate | 1 | 1 | 3 | 6 |
| | Total weight | 120 | 150 | 300 | 600 |

Compound (1i) (Scheme 6, R$^3$ = H, R$^4$ = CH$_3$) is micronized 5-(3,5-di-tert-butyl-4-hydroxyphenyl)-N-methyl-1H-triazole-4-sulfonamide.

Manufacturing Procedure

Mix Items 1, 2 and 3 in a suitable mixer for 15 minutes.
1. Granulate the powder mix from Step 1 with 20% polyvinyl pyrolidone K30 solution.
2. Dry the granulation from Step 2 at 50° C.
3. Pass the granulation from Step 3 through suitable milling equipment.
4. Add Item 5 to the milled granulation from Step 4 and mix for 3 minutes.
5. Compress the granulation from Step 5 on a suitable press.

Example 17

| Capsule Formulation | | | | | |
|---|---|---|---|---|---|
| Item | Ingredients | mg/tablet | | | |
| 1 | Compound 1i (R$^3$ = H, R$^4$ = CH$_3$) | 25 | 100 | 250 | 500 |
| 2 | Anhydrous Lactose | 123 | 148 | 0 | 0 |
| 3 | Corn Starch | 35 | 40 | 35 | 70 |

-continued

Capsule Formulation

| Item | Ingredients | mg/tablet | | | |
|---|---|---|---|---|---|
| 4 | Talc | 15 | 10 | 12 | 24 |
| 5 | Magnesium stearate | 2 | 2 | 3 | 6 |
| | Total weight | 200 | 300 | 300 | 600 |

Compound (1i) (Scheme 6, $R^3$ = H, $R^4$ = $CH_3$) is micronized 5-(3,5-di-tert-butyl-4-hydroxy-phenyl)-N-methyl-1H-triazole-4-sulfonamide.

Manufacturing Procedure

1. Mix Items 1, 2 and 3 in a suitable mixer for 30 minutes.
2. Add Items 4 and 5 and mix for 3 minutes.
3. Fill into a suitable capsule.

INCORPORATION BY REFERENCE

Patents and publications cited throughout this application reflect the levels of understanding of those skilled in the art to which the embodiments pertain. Said patents and publications are expressly incorporated herein in their entireties by reference.

EQUIVALENTS

Those skilled in the art will recognize, or be able to ascertain using no more than routine experimentation, many equivalents of the specific embodiments of the invention described herein. Such equivalents are intended to be encompassed by the following claims.

We claim:
1. A (1,2,3-triazolyl)sulfonyl derivative of formula (1)

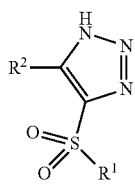

(1)

wherein
$R^1$ is aryl or a heterocyclic group which may be substituted at substitutable positions with amino, cyano, halo, nitro, alkyl, deuteroalkyl, halo(lower)alkyl, hydroxyalkyl, aminoalkyl, (cycloalkyl)alkyl, alkoxyalkyl, carboxyalkyl, (alkoxycarbonyl)alkyl, alkoxycarbonyl(amino) alkyl, (aminosulfonyl)alkyl, (alkylsulfonyl)alkyl, (arylsulfonyl)alkyl, arylalkyl, alkenyl, arylalkenyl, aryl, heteroaryl, hydroxy, alkoxy, acyloxy, aroyloxy, carboxy, alkylcarbonyl, alkoxycarbonyl, arylcarbonyl, arylalkylcarbonyl, aminocarbonyl, (heterocyclic)carbonyl, aryloxycarbonyl, (heterocyclic)oxycarbonyl, alkylsulfanyl, alkylsulfinyl, alkylsulfonyl, aminosulfonyl, (alkylcarbonyl)aminosulfonyl, arylsulfonyl, or lower alkylsulfonyloxy;
$R^1$ is also alkyl, deuteroalkyl, cyanoalkyl, halo(lower) alkyl, hydroxyalkyl, alkoxyalkyl, amino(lower)alkyl, arylalkyl, aryloxyalkyl, (alkylcarbonyl)alkyl, (aminocarbonyl)alkyl, (aminosulfonyl)alkyl, carboxyalkyl, alkoxycarbonylalkyl, alkoxycarbonyl(halo)alkyl, aminocarbonylalkyl, aminocarbonyl(halo)alkyl, heterocyclic(lower)alkyl, lower alkenyl, hydroxyl, lower alkoxy, deuteroalkoxy, haloalkoxy, or aryloxy;
$R^1$ is also amino as represented by $NR^3R^4$, wherein
$R^3$ is H, alkyl, deuteroalkyl, cyanoalkyl, halo(lower) alkyl, hydroxyalkyl, alkoxyalkyl, amino(lower)alkyl, aryl(lower)alkyl, alkylcarbonyl(lower)alkyl, aryl (lower)alkyl, lower alkenyl, hydroxy, lower alkoxy, deuteroalkoxy, aryloxy, or aminoalkoxy, and
$R^4$ is H, alkyl, deuteroalkyl, (cycloalkyl)alkyl, haloalkyl, hydroxyalkyl, alkoxyalkyl, alkylcarbonylalkyl, arylalkyl, aroylalkyl, aryloxyalkyl, heteroaryloxy(lower)alkyl, 5- or 6-membered heterocyclic alkyl, alkylcarbonylalkyl, alkoxycarbonylalkyl, aryloxycarbonylalkyl, heteroaryloxycarbonylalkyl, aminocarbonylalkyl, aminosulfonylalkyl, aminosulfonyl (amino)alkyl, carboxy(amino)alkyl, carboxy(halo) alkyl, alkoxycarbonyl(halo)alkyl, aminoalkyl, aminocarbonyl(halo)alkyl, heterocyclic(lower)alkyl, alkenyl, aryl substituted alkenyl, aryl, a 5- or 6-membered heterocyclic group, alkylcarbonyl, cycloalkylcarbonyl, alkoxycarbonyl, aminocarbonyl, arylcarbonyl, (heterocyclic)carbonyl, alkylsulfonyl, (cycloalkyl)alkylsulfonyl, arylsulfonyl, heteroarylsulfonyl, or aminosulfonyl, and
$R^3$ and $R^4$ taken together is optionally dialkylaminomethyleneamino, 1-(dialkylamino)ethylideneamino, 1-piperidinyl, morpholino, 3-thiazolidinyl, 1,2,3-triazol-1-yl, 2-piperidon-1-yl, or 2,6-piperidinedion-1-yl;
$R^2$ is aryl, heteroaryl or a heterocyclic group which may be substituted at substitutable positions with 1-5 radicals selected from a group comprising amino, halo, cyano, nitro, alkyl, (cycloalkyl)alkyl, cyanoalkyl, deuteroalkyl, haloalkyl, hydroxyalkyl, aminoalkyl, alkoxyalkyl, arylalkyl, aryloxyalkyl, alkylcarbonylalkyl, aminocarbonylalkyl, aminosulfonylalkyl, aminosulfonyl(amino)alkyl, carboxyalkyl, alkoxycarbonylalkyl, aryloxycarbonylalkyl, carboxy(amino)alkyl, alkoxycarbonyl(amino) alkyl, aryloxycarbonyl(amino)alkyl, aminocarbonyl (amino)alkyl, carboxy(halo)alkyl, alkoxycarbonyl (halo)alkyl, alkoxycarbonyl(hydroxy)alkyl, aryloxycarbonyl(halo)alkyl, aminocarbonyl(halo)alkyl, heterocyclic (lower)alkyl, (heterocyclic)oxyalkyl, halo (lower)alkyl, lower alkenyl, arylalkenyl, aryl, heteroaryl, hydroxy, carboxy, alkoxy, haloalkoxy, deuteroalkoxy, acyloxy, aryloxy, heteroaryloxy, alkylcarbonyl, arylcarbonyl, heteroarylcarbonyl, (heterocyclic)carbonyl, arylalkylcarbonyl, alkoxycarbonyl, aryloxycarbonyl, (heterocyclic)oxycarboxyl, aminocarbonyl, lower alkylsulfanyl, lower alkylsulfinyl, lower alkylsulfonyl, arylsulfonyl, heteroarylsulfonyl, (cycloalkyl)alkylsulfonyl, aminosulfonyl, (aminomethylene)sulfamoyl, or lower alkylsulfonyloxy.
2. A compound according to claim 1, wherein
$R^1$ is amino as in $NR^3R^4$, and wherein $R^3$ and $R^4$ are as defined, and where
$R^2$ is aryl or a heterocyclic group which may be unsubstituted or substituted at substitutable positions with 1-5 radicals selected from the group consisting of alkyl, deuteroalkyl, halo(lower)alkyl, halogen, cyano, amino, hydroxy, lower alkoxy, aminocarbonyl, lower alkylsulfonyl, and aminosulfonyl.
3. A compound according to claim 2, wherein
$R^2$ is 4-methylsulfonylphenyl, 4-(acetylsulfamoyl)phenyl, 3-indolyl, 4,6-di-tert-butyl-5-hydroxy-pyrimidin-2-yl, or 3,5-di-tert-butyl-4-hydroxyphenyl, R³ is H, hydroxy, lower alkyl, deuteroalkyl, lower alkoxy, aryloxy, halo(lower)alkyl, hydroxy(lower)alkyl, alkoxy(lower)alkyl, amino(lower)alkyl, lower alkenyl, arylcarbonyl, or alkylcarbonyl, and R⁴ is H, alkyl, deuteroalkyl, fluoroalkyl, hydroxyalkyl, alkoxyalkyl, aminoalkyl, arylalkyl, aryloxyalkyl, alkenyl, arylalkenyl, aryl, a heterocyclic group, or alkylcarbonyl.

4. A compound according to claim 3, wherein
R² is 3,5-di-tert-butyl-4-hydroxyphenyl,
R³ is H, and
R⁴ is methyl.

5. A compound according to claim 1, selected from the group consisting of
4-[4-(benzenesulfonyl)-1H-triazol-5-yl]-2,6-di-tert-butylphenol,
2,6-di-tert-butyl-4-[4-(2-hydroxyethylsulfonyl)-1H-triazol-5-yl]phenol,
5-(3,5-di-tert-butyl-4-hydroxy-phenyl)-N-hydroxy-N-methyl-1H-triazole-4-sulfonamide,
N-cyclopropyl-5-(3,5-di-tert-butyl-4-hydroxy-phenyl)-1H-triazole-4-sulfonamide,
2,6-di-tert-butyl-4-[4-(2-fluoroethylsulfonyl)-1H-triazol-5-yl]phenol,
5-(3,5-di-tert-butyl-4-hydroxy-phenyl)-N-(2,2,2-trifluoroethyl)-1H-triazole-4-sulfonamide,
5-(3,5-di-tert-butyl-4-hydroxy-phenyl)-N-methoxy-1H-triazole-4-sulfonamide,
2,6-di-tert-butyl-4-(4-methylsulfonyl-1H-triazol-5-yl)phenol,
5-(3,5-di-tert-butyl-4-hydroxy-phenyl)-1H-triazole-4-sulfonamide,
5-(3,5-di-tert-butyl-4-hydroxy-phenyl)-N-methyl-1H-triazole-4-sulfonamide,
3-[4-(benzenesulfonyl)-1H-triazol-5-yl]-1H-indole,
5-(3,5-di-tert-butyl-4-hydroxy-phenyl)-N-ethyl-1H-triazole-4-sulfonamide, and
4-(benzenesulfonyl)-5-(4-methylsulfonylphenyl)-1H-triazole.

6. A pharmaceutical composition containing an effective amount of a compound of the formula

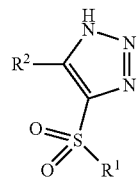

(1)

wherein
R¹ is aryl or a heterocyclic group which may be substituted at substitutable positions with amino, cyano, halo, nitro, alkyl, deuteroalkyl, halo(lower)alkyl, hydroxyalkyl, aminoalkyl, (cycloalkyl)alkyl, alkoxyalkyl, carboxyalkyl, (alkoxycarbonyl)alkyl, alkoxycarbonyl(amino)alkyl, (aminosulfonyl)alkyl, (alkylsulfonyl)alkyl, (arylsulfonyl)alkyl, arylalkyl, alkenyl, arylalkenyl, aryl, heteroaryl, hydroxy, alkoxy, acyloxy, aroyloxy, carboxy, alkylcarbonyl, alkoxycarbonyl, arylcarbonyl, arylalkylcarbonyl, aminocarbonyl, (heterocyclic)carbonyl, aryloxycarbonyl, (heterocyclic)oxycarbonyl, alkylsulfanyl, alkylsulfinyl, alkylsulfonyl, aminosulfonyl, (alkylcarbonyl)aminosulfonyl, arylsulfonyl, or lower alkylsulfonyloxy;

R¹ is also alkyl, deuteroalkyl, cyanoalkyl, halo(lower)alkyl, hydroxyalkyl, alkoxyalkyl, amino(lower)alkyl, arylalkyl, aryloxyalkyl, (alkylcarbonyl)alkyl, (aminocarbonyl)alkyl, (aminosulfonyl)alkyl, carboxyalkyl, alkoxycarbonylalkyl, alkoxycarbonyl(halo)alkyl, aminocarbonylalkyl, aminocarbonyl(halo)alkyl, heterocyclic(lower)alkyl, lower alkenyl, hydroxyl, lower alkoxy, deuteroalkoxy, haloalkoxy, or aryloxy;

R¹ is also amino as represented by NR³R⁴, wherein
R³ is H, alkyl, deuteroalkyl, cyanoalkyl, halo(lower)alkyl, hydroxyalkyl, alkoxyalkyl, amino(lower)alkyl, aryl(lower)alkyl, alkylcarbonyl(lower)alkyl, aryl(lower)alkyl, lower alkenyl, hydroxy, lower alkoxy, deuteroalkoxy, aryloxy, or aminoalkoxy, and R⁴ is H, alkyl, deuteroalkyl, (cycloalkyl)alkyl, haloalkyl, hydroxyalkyl, alkoxyalkyl, alkylcarbonylalkyl, arylalkyl, aroylalkyl, aryloxyalkyl, heteroaryloxy(lower)alkyl, 5- or 6-membered heterocyclic alkyl, alkylcarbonylalkyl, alkoxycarbonylalkyl, aryloxycarbonylalkyl, heteroaryloxycarbonylalkyl, aminocarbonylalkyl, aminosulfonylalkyl, aminosulfonyl(amino)alkyl, carboxy(amino)alkyl, carboxy(halo)alkyl, alkoxycarbonyl(halo)alkyl, aminoalkyl, aminocarbonyl(halo)alkyl, heterocyclic(lower)alkyl, alkenyl, aryl substituted alkenyl, aryl, a 5- or 6-membered heterocyclic group, alkylcarbonyl, cycloalkylcarbonyl, alkoxycarbonyl, aminocarbonyl, arylcarbonyl, (heterocyclic)carbonyl, alkylsulfonyl, (cycloalkyl)alkylsulfonyl, arylsulfonyl, heteroarylsulfonyl, or aminosulfonyl, and R³ and R⁴ taken together is optionally dialkylaminomethyleneamino, 1-(dialkylamino)ethylideneamino, 1-piperidinyl, morpholino, 3-thiazolidinyl, 1,2,3-triazol-1-yl, 2-piperidon-1-yl, or 2,6-piperidinedion-1-yl;

R² is aryl, heteroaryl or a heterocyclic group which may be substituted at substitutable positions with 1-5 radicals selected from a group comprising amino, halo, cyano, nitro, alkyl, (cycloalkyl)alkyl, cyanoalkyl, deuteroalkyl, haloalkyl, hydroxyalkyl, aminoalkyl, alkoxyalkyl, arylalkyl, aryloxyalkyl, alkylcarbonylalkyl, aminocarbonylalkyl, aminosulfonylalkyl, aminosulfonyl(amino)alkyl, carboxyalkyl, alkoxycarbonylalkyl, aryloxycarbonylalkyl, carboxy(amino)alkyl, alkoxycarbonyl(amino)alkyl, aryloxycarbonyl(amino)alkyl, aminocarbonyl(amino)alkyl, carboxy(halo)alkyl, alkoxycarbonyl(halo)alkyl, alkoxycarbonyl(hydroxy)alkyl, aryloxycarbonyl(halo)alkyl, aminocarbonyl(halo)alkyl, heterocyclic (lower)alkyl, (heterocyclic)oxyalkyl, halo(lower)alkyl, lower alkenyl, arylalkenyl, aryl, heteroaryl, hydroxy, carboxy, alkoxy, haloalkoxy, deuteroalkoxy, acyloxy, aryloxy, heteroaryloxy, alkylcarbonyl, arylcarbonyl, heteroarylcarbonyl, (heterocyclic)carbonyl, arylalkylcarbonyl, alkoxycarbonyl, aryloxycarbonyl, (heterocyclic)oxycarboxyl, aminocarbonyl, lower alkylsulfanyl, lower alkylsulfinyl, lower alkylsulfonyl, arylsulfonyl, heteroarylsulfonyl, (cycloalkyl)alkylsulfonyl, aminosulfonyl, (aminomethylene)sulfamoyl, or lower alkylsulfonyloxy, and an inert carrier.

7. A pharmaceutical composition according to claim 6 wherein a compound of formula (1) is selected from the group consisting of
4-[4-(benzenesulfonyl)-1H-triazol-5-yl]-2,6-di-tert-butylphenol,
2,6-di-tert-butyl-4-[4-(2-hydroxyethylsulfonyl)-1H-triazol-5-yl]phenol, 5-(3,5-di-tert-butyl-4-hydroxy-phenyl)-N-hydroxy-N-methyl-1H-triazole-4-sulfonamide,
N-cyclopropyl-5-(3,5-di-tert-butyl-4-hydroxy-phenyl)-1H-triazole-4-sulfonamide,
2,6-di-tert-butyl-4-[4-(2-fluoroethylsulfonyl)-1H-triazol-5-yl]phenol,
5-(3,5-di-tert-butyl-4-hydroxy-phenyl)-N-(2,2,2-trifluoroethyl)-1H-triazole-4-sulfonamide,
5-(3,5-di-tert-butyl-4-hydroxy-phenyl)-N-methoxy-1H-triazole-4-sulfonamide,
2,6-di-tert-butyl-4-(4-methylsulfonyl-1H-triazol-5-yl)phenol,
5-(3,5-di-tert-butyl-4-hydroxy-phenyl)-1H-triazole-4-sulfonamide,
5-(3,5-di-tert-butyl-4-hydroxy-phenyl)-N-methyl-1H-triazole-4-sulfonamide,
3-[4-(benzenesulfonyl)-1H-triazol-5-yl]-1H-indole,
5-(3,5-di-tert-butyl-4-hydroxy-phenyl)-N-ethyl-1H-triazole-4-sulfonamide, and
4-(benzenesulfonyl)-5-(4-methylsulfonylphenyl)-1H-triazole.

8. A pharmaceutical composition according to claim 7 wherein the compound of formula (1) is 5-(3,5-di-tert-butyl-4-hydroxy-phenyl)-N-methyl-1H-triazole-4-sulfonamide.

9. A pharmaceutical composition according to claim 6 for the treatment of a host whose disease is caused by inflammation, or where an inflammatory component is the underlying cause of the disease, or for the prevention of such a pathological condition.

10. A pharmaceutical composition according to claim 9 where the compound of formula (1) is 5-(3,5-di-tert-butyl-4-hydroxy-phenyl)-N-methyl-1H-triazole-4-sulfonamide.

11. A compound of the formula

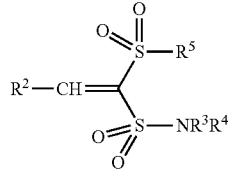

(2b)

wherein
$R^2$ is selected from aryl or a heterocyclic group which may be substituted at substitutable positions with 1-5 radicals selected from the group consisting of hydroxy, halo, carboxy, cyano, nitro, amino, alkyl, aryl, (cycloalkyl)alkyl, cyanoalkyl, halo(lower)alkyl, hydroxyalkyl, alkoxyalkyl, amino(lower)alkyl, aryl(lower)alkyl, aryloxy(lower)alkyl, (alkylcarbonyl)alkyl, (aminocarbonyl)alkyl, (aminosulfonyl)alkyl, (aminosulfonylamino)alkyl, carboxyalkyl, alkoxyalkyl, (alkoxycarbonyl)alkyl, (aryloxycarbonyl)alkyl, carboxy(halo)alkyl, alkoxycarbonyl(halo)alkyl, aryloxycarbonyl(halo)alkyl, heterocyclic(lower)alkyl, aminosulfonylamino, lower alkylsulfonyloxy, lower alkoxy, aryloxy, alkylcarbonyl, arylcarbonyl, (heterocyclic)carbonyl, alkoxycarbonyl, aryloxycarbonyl, (heterocyclic)oxycarbonyl, aminocarbonyl, lower alkylsulfanyl, lower alkylsulfinyl, lower alkylsulfonyl, (cycloalkyl)sulfonyl, aminosulfonyl, and N-(aminomethylene)sulfamoyl, $R^3$ is H, hydroxy, alkyl, aryl, deuteroalkyl, cyanoalkyl, halo(lower)alkyl, hydroxyalkyl, alkoxyalkyl, amino(lower)alkyl, aryl(lower)alkyl, acyl(lower)alkyl, aryl(lower)alkyl, lower alkenyl, lower alkoxy, deuteroalkoxy, or aryloxy, $R^4$ is H, alkyl, deuteroalkyl, (cycloalkyl)alkyl, halooalkyl, hydroxyalkyl, alkoxyalkyl, aminoalkyl, arylalkyl, aryloxyalkyl, (heterocyclic)alkyl, arylalkenyl, alkylsulfonyl, arylsulfonyl, aminosulfonyl, carboxy, alkylcarbonyl, (cycloalkyl)alkylcarbonyl, alkoxycarbonyl, aminocarbonyl, arylcarbonyl, (heterocyclic)carbonyl, (alkylcarbonyl)alkyl, (alkoxycarbonyl)alkyl, (aminocarbonyl)alkyl, (aminosulfonyl)alkyl, aminosulfonyl(amino)alkyl, carboxy(halo)alkyl, alkoxycarbonyl(halo)alkyl, aminocarbonyl(halo)alkyl, heterocyclic(lower)alkyl, alkenyl, or a heterocyclic group, and $R^3$ and $R^4$ taken together is aminomethyleneamino, 1-aminoethylideneamino, 1-piperidinyl, morpholino, 3-thiazolidinyl, 1,2,3-triazol-1-yl, and 2-piperidon-1-yl, or 2,6-piperidinedion-1-yl, and $R^5$ is alkyl or aryl.

12. A compound according to claim 11, wherein
$R^2$ is aryl or a heterocyclic group which may be substituted at substitutable positions with 1-5 radicals selected from the group consisting of alkyl, deuteroalkyl, haloalkyl, halo, lower alkoxy, lower alkylthio, lower alkylsulfinyl, lower alkylsulfonyl, aminosulfonyl, aminosulfonylamino, hydroxy, cyano, nitro, amino, and aminocarbonyl, and
$R^5$ is lower alkyl or aryl.

13. A compound according to claim 12, wherein
$R^2$ is 3,5-di-tert-butyl-4-hydroxyphenyl,
$R^3$ is H,
$R^4$ is H, methyl, or deuteromethyl, and
$R^5$ is phenyl.

14. A compound according to claim 13, wherein
$R^2$ is 3,5-di-tert-butyl-4-hydroxyphenyl,
$R^3$ and $R^4$ are H, and
$R^5$ is phenyl.

* * * * *